(12) United States Patent
Kishima et al.

(10) Patent No.: US 8,598,541 B2
(45) Date of Patent: Dec. 3, 2013

(54) FLUORESCENT IMAGE OBTAINING DEVICE, FLUORESCENT IMAGE OBTAINING METHOD AND FLUORESCENT IMAGE OBTAINING PROGRAM

(75) Inventors: Koichiro Kishima, Kanagawa (JP); Yu Hirono, Tokyo (JP); Nobuhiro Hayashi, Kanagawa (JP); Takamichi Yamakoshi, Tokyo (JP); Nobuhiro Kihara, Kanagawa (JP); Takashi Yamamoto, Tokyo (JP); Fumiyasu Suzuki, Saitama (JP); Ryu Narusawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 180 days.

(21) Appl. No.: 12/868,187

(22) Filed: Aug. 25, 2010

(65) Prior Publication Data

US 2011/0049389 A1    Mar. 3, 2011

(30) Foreign Application Priority Data

Aug. 31, 2009   (JP) ................................ P2009-200891
Oct. 23, 2009   (JP) ................................ P2009-244874

(51) Int. Cl.
*G01J 1/58*    (2006.01)

(52) U.S. Cl.
USPC .................................... 250/459.1; 250/458.1

(58) Field of Classification Search
USPC ....................................................... 250/459.1
See application file for complete search history.

(56) References Cited

U.S. PATENT DOCUMENTS

| 5,097,135 A * | 3/1992 | Makino et al. ............. 250/461.1 |
| 5,986,271 A * | 11/1999 | Lazarev et al. ............. 250/458.1 |
| 2002/0090120 A1 | 7/2002 | Wetzel et al. |
| 2003/0151735 A1 * | 8/2003 | Blumenfeld et al. ........... 356/73 |
| 2004/0156109 A1 | 8/2004 | Hoover et al. |
| 2006/0249689 A1 * | 11/2006 | Eustergerling et al. .... 250/458.1 |
| 2007/0134712 A1 * | 6/2007 | Yonekawa et al. ................. 435/6 |
| 2007/0274580 A1 * | 11/2007 | Ntziachristos et al. ........ 382/131 |
| 2009/0066934 A1 * | 3/2009 | Gao et al. ........................ 356/73 |
| 2009/0146077 A1 * | 6/2009 | Moy et al. .................. 250/458.1 |
| 2009/0194693 A1 * | 8/2009 | Klunder et al. ............... 250/332 |

FOREIGN PATENT DOCUMENTS

| CA | 2444413 | 4/2005 |
| JP | HEI10-206745 | 8/1998 |
| JP | 2003-222801 | 8/2003 |
| JP | 2004-301561 | 10/2004 |
| JP | 2007-310231 | 11/2007 |
| WO | 2008092075 | 7/2008 |
| WO | 2009016548 | 2/2009 |
| WO | WO 2009016548 A2 * | 2/2009 |

OTHER PUBLICATIONS

European Patent Office, Extended European Search Report issued in connection with European Patent Application No. 10008146.2 on Nov. 4, 2011. (9 pages).

Japanese Office Action issued Jun. 25, 2013 for corresponding Japanese Appln. No. 2009-244874.

* cited by examiner

*Primary Examiner* — Marcus Taningco
(74) *Attorney, Agent, or Firm* — K&L Gates LLP

(57) ABSTRACT

A fluorescent image obtaining device includes a light source that irradiates light such that a fluorescent material marked on a target in a biological sample lies in a non-excited state and a fluorescent material marked on a control with the target lies in an excited state, and an imaging unit that takes an image including the entire biological sample.

17 Claims, 19 Drawing Sheets

FIG. 22
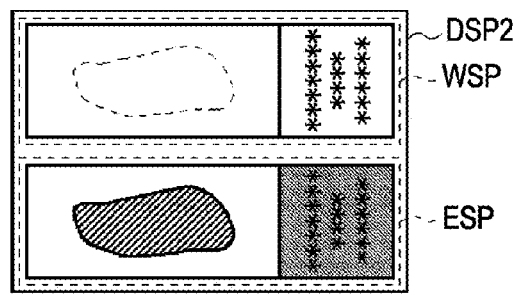
FIG. 23A    FIG. 23B
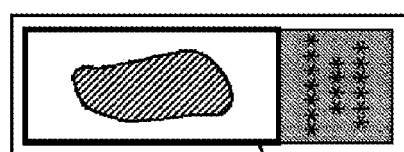 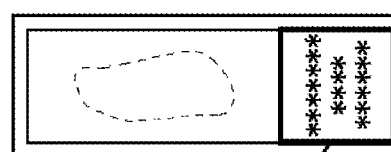
FIG. 23C
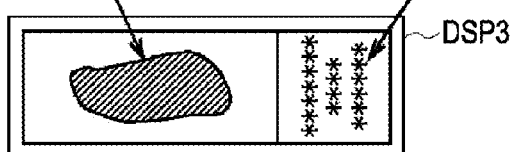

FLUORESCENT IMAGE OBTAINING DEVICE, FLUORESCENT IMAGE OBTAINING METHOD AND FLUORESCENT IMAGE OBTAINING PROGRAM

CROSS REFERENCES TO RELATED APPLICATIONS

The present application claims priority to Japanese Priority Patent Application JP 2009-200891 filed in the Japan Patent Office on Aug. 31, 2009 and Japanese Priority Patent Application JP 2009-244874 filed in the Japan Patent Office on Oct. 23, 2009, the entire contents of which are hereby incorporated by reference.

BACKGROUND

The present application relates to a fluorescent image obtaining device, a fluorescent image obtaining method and a fluorescent image obtaining program, which is suitable for an application to, for example, a field for observing tissue slices.

In the related art, biological samples such as tissue slices or the like usable in the field of pathology are fixed to a slide glass and undergo a predetermined stain. Generally, if a period for maintaining the biological sample is lengthened, the biological sample itself is deteriorated, the stain performed for the biological sample is discolored, and the visibility in a microscope for the biological sample is lowered. In addition, the biological samples may be diagnosed in other places than facilities which have created the biological samples such as hospitals or the like, and the biological samples are typically transported by mail which takes a constant time.

In consideration of such problems, there has been proposed a device which stores the biological sample as image data (for example, refer to Japanese Unexamined Patent Application Publication No. 2003-222801).

SUMMARY

In addition, in the pathology, it is firstly determined whether or not malignant tumors are present in terms of morphology by using tissue slices which have undergone an HE (Hematoxylin-Eosin) stain. Also, when a malignant tumor is found or a part where the presence of the malignant tumor is suspected is found, the presence/absence, kind, and degree of progress of a malignant tumor etc., are secondarily determined by using the biological sample having undergone the fluorescent stain.

Such pathology can use an enlarged image of high definition, which is obtained by enlarging the biological sample at a certain magnification. A device for obtaining the enlarged image of a high definition images the entire slide glass where, for example, the biological sample is disposed, and a region in which the biological sample is present is designated based on the image. A plurality of images enlarging the designated region at a specific magnification is consecutively obtained, and the enlarged image of high definition is obtained by combining the plurality of consecutive images.

However, since the fluorescently stained biological sample is colorless and clear in a non-excited state, it is difficult to specify the fluorescently stained biological sample in a non-excited state on the slide glass. For this reason, if an enlarged image of high definition is to be obtained without knowing the position of the biological sample, the entire region where the biological sample is positioned is imaged, and thus the amount of data becomes massive.

Meanwhile, it is also thought to image the entire slide glass by exciting the fluorescently stained biological sample. However, a fluorescent material marked on a target in the biological sample is particularly easily discolored.

Therefore, there are problems in that the discoloration of the fluorescent material marked on the target in the biological sample is viewed when the entire slide glass is imaged, and thereby the image quality is deteriorated by the discoloration of the fluorescent material in an enlarged image of high definition obtained after imaging the entire slide glass.

It is desirable to provide a fluorescent image obtaining device, a fluorescent image obtaining method and a fluorescent image obtaining program, capable of obtaining images for the whole of a fluorescently stained biological sample without deteriorating the image quality.

According to an embodiment, there is provided a fluorescent image obtaining device including a light source that irradiates light such that a fluorescent material marked on a target in a biological sample lies in a non-excited state and a fluorescent material marked on a control with the target lies in an excited state, and an imaging unit that takes an image including the entire biological sample.

In addition, according to an embodiment, there is provided a fluorescent image obtaining method including the steps of irradiating light from a light source such that a fluorescent material marked on a target in a biological sample lies in a non-excited state and a fluorescent material marked on a control with the target lies in an excited state, and taking an image including the entire biological sample by an imaging unit.

Further, according to an embodiment, there is provided a fluorescent image obtaining program enabling a computer to execute the steps of irradiating light from a light source such that a fluorescent material marked on a target in a biological sample lies in a non-excited state and a fluorescent material marked on a control with the target lies in an excited state, and taking an image including the entire biological sample by an imaging unit.

Therefore, since the fluorescent material marked on the target in the biological sample lies in the non-excited state and only the fluorescent material marked on the control with the target lies in the excited state, it is possible to prevent the discoloration of the fluorescent material marked on the target in the biological sample and to obtain the image of the entire region where the biological sample is disposed.

According to the present application as described above, since the fluorescent material marked on the target in the biological sample lies in the non-excited state and only the fluorescent material marked on the control with the target lies in the excited state, it is possible to prevent the discoloration of the fluorescent material marked on the target in the biological sample and to obtain the image of the entire region where the biological sample is disposed, and thereby there is implementation of a fluorescent image obtaining device, a fluorescent image obtaining method, and a fluorescent image obtaining program, capable of obtaining an image of the fluorescently stained biological sample without deterioration in the image quality.

Additional features and advantages are described herein, and will be apparent from the following Detailed Description and the figures.

BRIEF DESCRIPTION OF THE FIGURES

FIG. 22 is an outlined line diagram illustrating a dark field thumbnail image (2) according to the second embodiment.

FIGS. 23A to 23C are outlined line diagrams illustrating dark field thumbnail images (3) according to the second embodiment.

DETAILED DESCRIPTION

Figure 1:
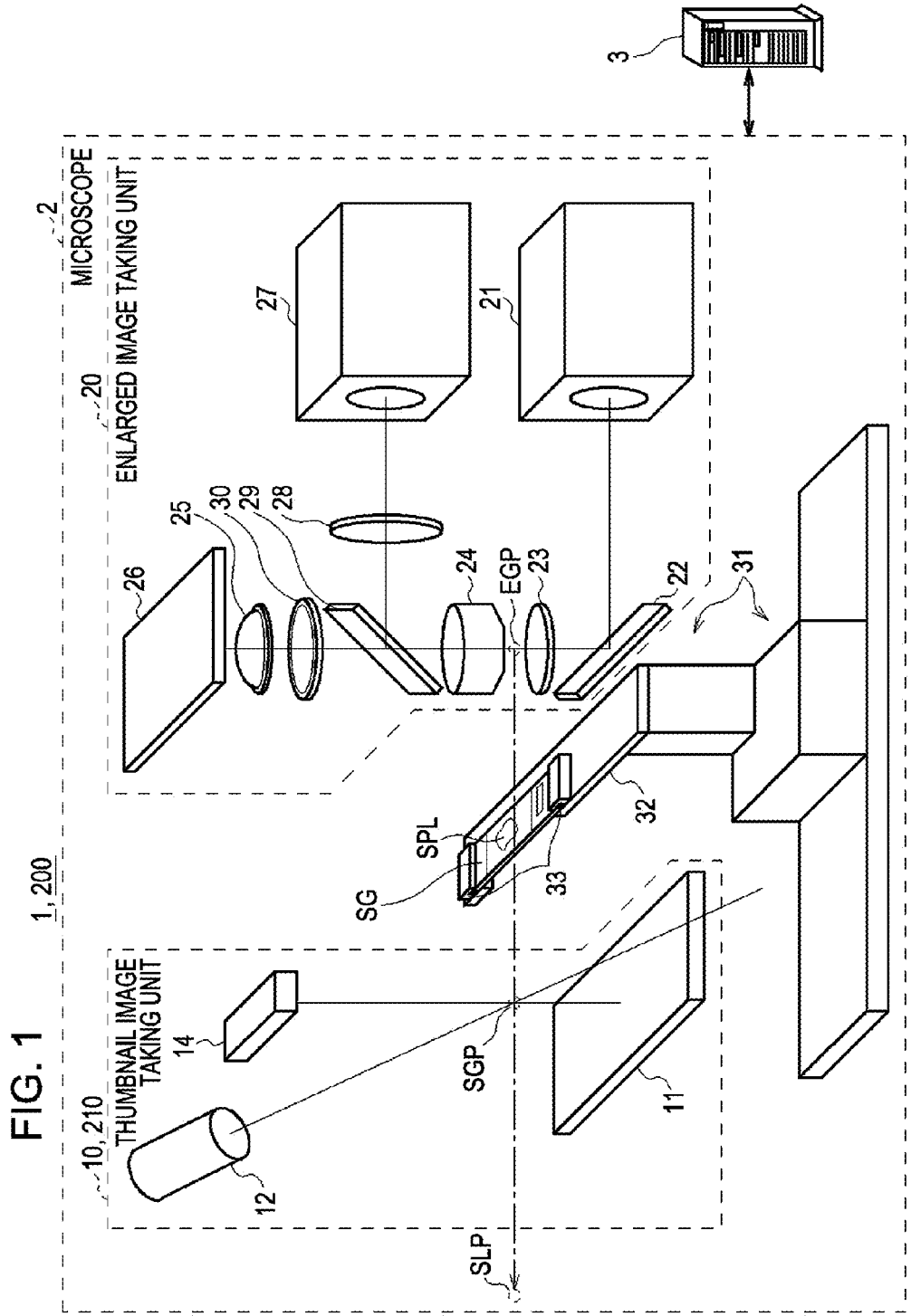
FIG. 1 is a diagram schematically illustrating a configuration of a biological sample image obtaining device.

The present application is described below in detail with reference to the drawings according to an embodiment. The detailed description is provided as follows:

1. First Embodiment
1-1. Configuration of biological sample image obtaining device
1-2. Configuration of thumbnail image taking unit
1-3. Configuration of data processing unit
1-4. Detailed content of biological sample image obtaining processing
1-5. Operation and effect
1-6. Other embodiments
2. Second Embodiment
2-1. Configuration of thumbnail image taking unit
2-2. Detailed content of biological sample image obtaining processing
2-3. Operation and effect
2-4. Other embodiments
3. Third Embodiment
3-1. Functional configuration of CPU
3-2. Detailed content of biological sample image obtaining processing
3-3. Operation and effect
3-4. Other embodiments 1. First Embodiment 1-1. Configuration of Biological Sample Image Obtaining Device FIG. 1 shows a biological sample image obtaining device 1 according to an embodiment. The biological sample image obtaining device 1 includes a microscope 2 and a data processing unit 3.

The microscope 2 has a thumbnail image taking unit 10 which takes an image of the entire slide glass SG where a sample for a living object (hereinafter, referred to as a "biological sample") SPL is disposed, and an enlarged image taking unit 20 which takes an enlarged image of the biological sample SPL. The microscope 2 has a case (not shown) covering its entirety so that an external light is not incident therein.

In addition, the microscope 2 has a stage 31 (hereinafter, referred to as a "movable stage") capable of moving a slide holder 32, supporting the slide glass SG, in the parallel direction and orthogonal direction (xyz axial directions).

The microscope 2 changes a bright field mode or a dark field mode, takes an image of the entire slide glass SG by the thumbnail image taking unit 10, and takes an enlarged image of the biological sample SPL by the enlarged image taking unit 20.

The biological sample SPL means that tissue slices of tissues such as connective tissues, for example, blood or the like, epithelial tissues, or both of the tissues, etc., or smear cells, are fixed to the slide glass SG by using a predetermined fixing method, and the tissue slices or the smear cells are stained if necessary. This stain includes not only general stains represented by an HE stain, a Giemsa stain, Papanicolaou stain, or the like, but also fluorescent stains such as a FISH (Fluorescence In-Situ Hybridization) or an enzyme labeled antibody method, or the like.

In the microscope 2, the slide holder 32 is moved to a slide glass loading position SLP placed near an attachment/detachment hole (not shown) by the movable stage 31 when the slide glass SG is attached/detached to/from the slide holder 32. Thereafter, the slide glass SG is installed in or removed from the slide holder 32.

The slide holder 32 is substantially formed in the character U shape because it is shorter than the long side of the slide glass SG in the longitudinal direction and has an opening almost the same as the short side of the slide glass SG in the transverse direction.

Therefore, when the slide glass SG is installed in the slide holder 32, both ends of the slide glass SG are supported by the slide holder 32 in the long direction and thus both ends are interposed between the slide holder 32 and a slide glass pressure 33 and are supported.

The thumbnail image taking unit 10 takes an image of the entire slide glass SG as described later in detail after the slide glass SG is moved to a thumbnail image taking position SGP according to the movement of the movable stage 31. In addition, in FIG. 1, for convenience of description, only a portion of the thumbnail image taking unit 10 is shown.

After the slide glass SG is moved to an enlarged image taking position EGP positioned between a bright field filter 23 and an object lens 24 by the movable stage 31, the enlarged image taking unit 20 takes an enlarged image of the biological sample SPL.

In detail, in the bright field mode, the enlarged image taking unit 20 reflects light emitted from a white light source 21 by a reflection mirror 22 and then irradiates the light from one side of the slide holder 32 to the biological sample SPL via the bright field filter 23.

The enlarged image taking unit 20 enlarges an image of the biological sample SPL part obtained by the light at a predetermined magnification, by using the object lens 24 and an imaging lens 25 provided at the other side of the slide holder 32. The enlarged image taking unit 20 forms the image enlarged by the object lens 24 and the imaging lens 25 on an imaging area of an imaging element 26.

In relation thereto, the enlarged image taking unit 20 is configured in the bright field mode in such a manner that a dichroic mirror 29 and an emission filter 30 are excluded from a light path between the object lens 24 and the imaging lens 25.

The data processing unit 3 drives the white light source 21 in the bright field mode, obtains an image of the biological sample SPL in a bright field state as a bright field enlarged image by using the imaging element 26, and stores it as data of a predetermined format (hereinafter, referred to as "bright field enlarged image data").

Meanwhile, the enlarged image taking unit 20 illuminates light rays from an excitation light source 27 which is constituted by, for example, a mercury lamp, and transmits only a light ray with excitation wavelength for fluorescent stain out of the light rays through an excitation filter 28.

The light ray (hereinafter, also referred to as an "excitation light") transmitting the excitation filter 28 is reflected by the dichroic mirror 29 provided between the object lens 24 and the imaging lens 25 and then reaches the object lens 24. The enlarged image taking unit 20 collects the excitation light on the biological sample SPL disposed on the slide glass SG by using the object lens 24.

When the fluorescent stain has been performed for the biological sample SPL, the fluorescent material emits light by the excitation light, and the light obtained by the emission (hereinafter, referred to as a "coloring light") transmits the dichroic mirror 29 via the object lens 24. The coloring light reaches the imaging lens 25 via the emission filter 30 provided between the dichroic mirror 29 and the imaging lens 25.

The enlarged image taking unit 20 enlarges an image by the coloring light by using the object lens 24 and the imaging lens 25 and absorbs light (hereinafter, also referred to as "outside light") other than the coloring light by using the emission filter 30. The enlarged image taking unit 20 forms an image by the coloring light where the outside light is lost, on the imaging area of the imaging element 26.

In the dark field mode, the data processing unit 3 drives the excitation light source 27, obtains an image of the biological sample SPL in a dark field state as a dark field enlarged image by using the imaging element 26, and stores it as data of a predetermined format (hereinafter, also referred to as "dark field enlarged image data").

In this way, the biological sample image obtaining device 1 can store the biological sample SPL disposed on the slide glass SG as the bright field enlarged image data and dark field enlarged image data.

Accordingly, the biological sample image obtaining device 1 can store for a long time the generally stained or fluorescently stained biological sample SPL without deterioration in the states such as the fixation or stain or the like as compared with when the slide glass SG itself is stored.

1-2. Configuration of Thumbnail Image Taking Unit

Figure 2:
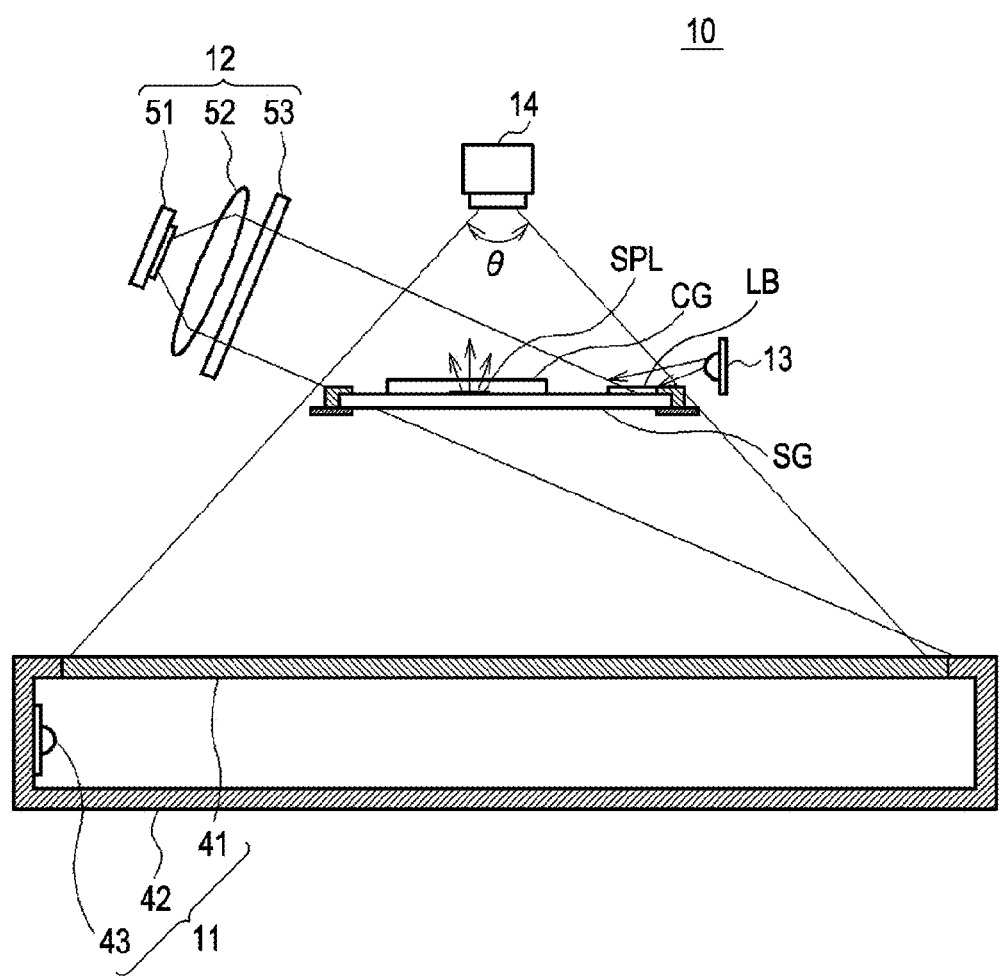
FIG. 2 is a diagram schematically illustrating a configuration of a thumbnail image taking unit.

The thumbnail image taking unit 10 includes, as shown in FIG. 2, a bright field illumination system 11, a dark field illumination system 12, a label illumination system 13, and a thumbnail camera 14.

The thumbnail image taking unit 10 images the entire slide glass SG after the slide glass SG is moved to the thumbnail image taking position SEP positioned between the bright field illumination system 11 and the thumbnail camera 14 by the movable stage 31.

The thumbnail image taking unit 10 illuminates light from the bright field illumination system 11 in the bright field mode. The bright field illumination system 11 is provided opposite to the thumbnail camera 14 with the slide glass SG interposed therebetween, and irradiates an illumination light to the biological sample SPL.

Further in detail, the bright field illumination system 11 has a white LED 43 inside an illumination box 42 which is roughly cuboid of which the upper face is a diffusion plate 41 and the center is empty. If light emitted from the white LED 43 is reflected via the inner space of the illumination box 42 to reach the diffusion plate 41, it is diffused by the diffusion plate 41 to be emitted to the slide glass SG side as substantially uniform light and is irradiated to the entire surface of the slide glass SG.

The label illumination system 13 is provided at one end of the slide glass SG and irradiates light to a label LB where attendant information is written or barcodes indicating the attendant information are written. The attendant information includes a sample number of the slide glass SG, the name of the person the biological sample SPL was collected from, the sex of the person, the age of the person, the date of the collection, the staining method, and so forth.

The thumbnail camera 14 is set to a predetermined angle of view θ capable of imaging the entire slide glass SG. The thumbnail camera 14 forms an image of the entire slide glass SG including the biological sample SPL and the label LB on the imaging area of the thumbnail camera 14 when the biological sample SPL is generally stained.

The data processing unit 3 drives the bright field illumination system 11 in the bright field mode. The data processing unit 3 obtains an image of the entire slide glass SG in the bright field state as a bright field thumbnail image by using the thumbnail camera 14, and stores it as data of a predetermined format (hereinafter, referred to as "bright field thumbnail image data").

Figure 3:
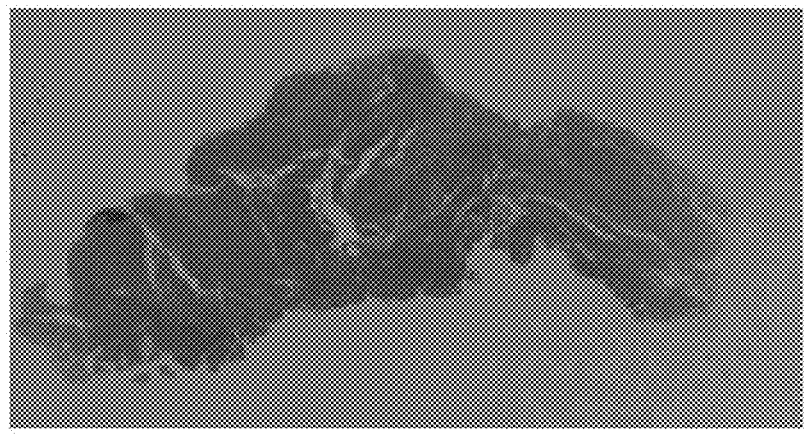
FIG. 3 is a diagram illustrating a bright field thumbnail image.

Here, FIG. 3 shows as an example the biological sample SPL part in the bright field thumbnail image in the case where the biological sample SPL has undergone the HE stain which is a kind of general stain.

In this way, the thumbnail image taking unit 10 can take the bright field thumbnail image where an outer shape of the HE stained biological sample SPL can be recognized clearly.

Also, since the fluorescently stained biological sample SPL is nearly clear in the non-excited state, when it is imaged in the bright field mode, the image thereof is not taken.

Here, an example of a fluorescently stained biological sample SPL will be taken. Upon determination of whether or not the protein HER2 (Human Epithelial growth factor Receptor type 2) is present in mammary gland tissues, the biological sample SPL is stained by, for example, PathVysion of HER-2DNA probe kit made by Abbott Corporation, as a reagent.

The reagent contains probes which respectively perform hybridization for the gene HER2/neu coding the protein HER2 and for the alpha satellite DNA sequence of the centromere area of the chromosome No. 17.

When the excitation light for exciting the probes is irradiated to the biological sample SPL, the probes are excited to emit fluorescence. At this time, the probes which perform hybridization for the gene HER2/neu and the alpha satellite DNA sequence respectively emit the fluorescence with different wavelengths.

Also, in the molecular diagnosis, it is determined whether or not the gene HER2/neu is increased based on the ratio of the number of the gene HER2/neu and the alpha satellite DNA sequence inside the cell nucleus.

Therefore, the biological sample SPL is stained by DAPI (4',6-diamidino-2-pheylindole) which is a reagent for staining the cell nucleus along with PathVysion, in order to determine the number of the gene HER2/neu and the alpha satellite DNA sequence inside the cell nucleus.

The reagent DAPI is excited by light with a wavelength of 365 nm different from the wavelengths of the probes which perform hybridization for the gene HER2/neu and the alpha satellite DNA sequence.

Thereby, in the dark field mode, the thumbnail image taking unit 10 emits, to the slide glass SG, light with the wavelength of about 365 nm from an excitation light source 51 of the dark field illumination system 12 provided at the same side as the thumbnail camera 14.

The light emitted from the excitation light source 51 is converted into a parallel light by a condenser 52 and is irradiated to the region where the biological sample SPL is disposed as the excitation light via an excitation filter 62. In relation thereto, the region where the biological sample SPL is disposed is, for example, a region where there is a cover glass CG which pinches the biological sample SPL on the slide glass SG along with the slide glass SG.

The excitation light source 51 irradiates the light with the wavelength of about 365 nm to the region where the biological sample SPL is disposed, with a tilted angle larger than about a half of the angle of view θ of the thumbnail camera 14 with respect to the optical axis of the thumbnail camera 14.

In addition, the excitation light source 51 irradiates the excitation light to a range exceeding the imaging range of the thumbnail camera 14 in the diffusion plate 41.

When the biological sample SPL is fluorescently stained, the thumbnail camera 14 forms, on the imaging area of the thumbnail camera 14, an image of the entire slide glass SG where DAPI in the biological sample SPL part is excited by the light emitted from the excitation light source 51 to emit fluorescence.

The data processing unit 3 drives the dark field illumination system 12 in the dark field mode. In addition, the data processing unit 3 obtains an image of the entire slide glass SG in the dark field state as a dark field thumbnail image by using the thumbnail camera 14, and stores it as data of a predetermined format (hereinafter, also referred to as "dark field thumbnail image data").

Figure 4:
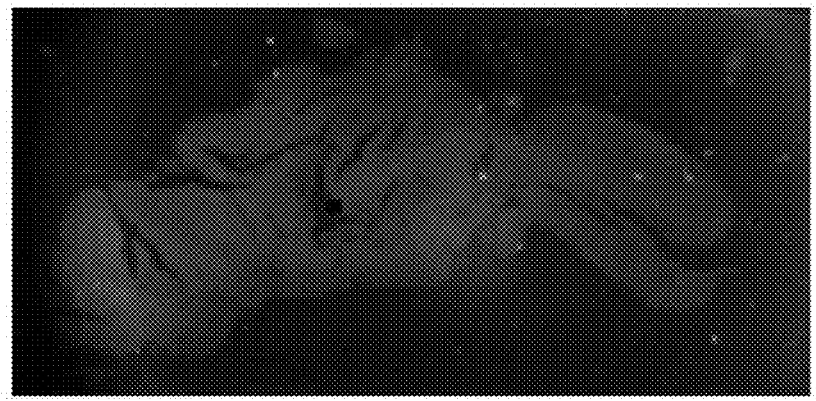
FIG. 4 is a diagram illustrating a dark field thumbnail image.

Here, FIG. 4 shows as an example a region part where the biological sample SPL in the dark field thumbnail image is disposed in the case where the biological sample SPL is stained by PathVysion of HER-2DNA probe kit and DAPI as the fluorescent stain.

In this way, the thumbnail image taking unit 10 can take the dark field thumbnail image where an outer shape of the DAPI stained biological sample SPL can be recognized clearly.

1-3. Configuration of the Data Processing Unit

Figure 5:
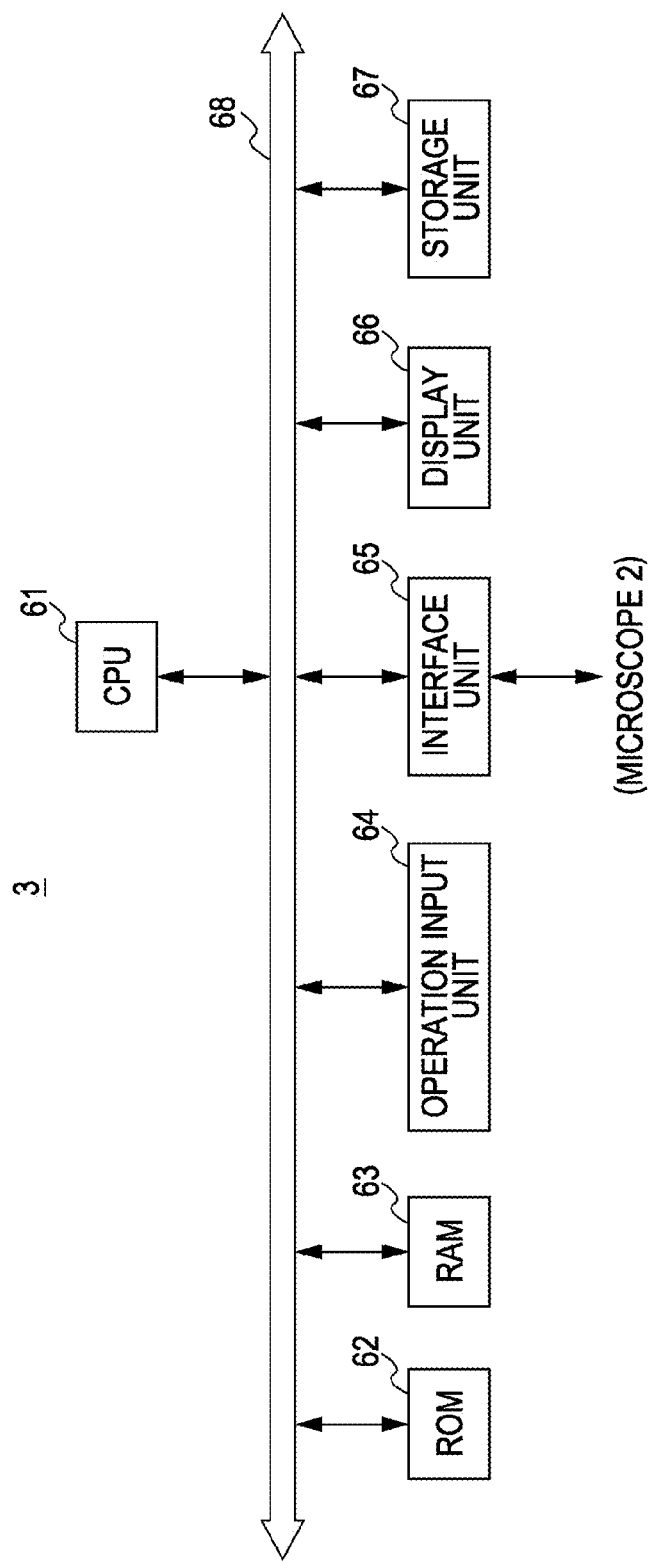
FIG. 5 is a block diagram illustrating a configuration of a data processing unit.

Next, a configuration of the data processing unit 3 will be described. The data processing unit 3 is configured by connecting various kinds of hardware to a CPU (central processing unit) 61 which performs controls, as shown in FIG. 5.

In detail, there are connections of an ROM (read only memory) 62, an RAM (random access memory) 63 which is a work memory of the CPU 61, an operation input unit 64 which inputs commands in response to operations by a user, an interface unit 65, a display unit 66, and a storage unit 67, via a bus 68.

The ROM 62 stores programs for executing various kinds of processings. The interface unit 65 is connected to the microscope 2 (FIG. 1).

The display unit 66 employs a liquid crystal display, an EL (electroluminescence) display, a plasma display, or the like. The storage unit 67 employs a magnetic disc represented by a HD (hard disc), a semiconductor memory, an optical disc, or the like. A portable memory such as a USB (universal serial bus) memory, a CF (compact flash) memory, or the like may be employed.

The CPU 61 develops a program corresponding to a command from the operation input unit 64, of the plurality of programs stored in the ROM 62, in the RAM 63, and properly controls the display unit 66 and the storage unit 67 in accordance with the developed program.

The CPU 61 properly controls each part of the microscope 2 via the interface unit 65 in accordance with the developed program.

1-4. Detailed Contents of Biological Sample Image Obtaining Processing

When receiving a command for obtaining an image of the biological sample SPL from the operation input unit 64, the CPU 61 develops a program corresponding to the obtaining command in the RAM 63.

Figure 6:
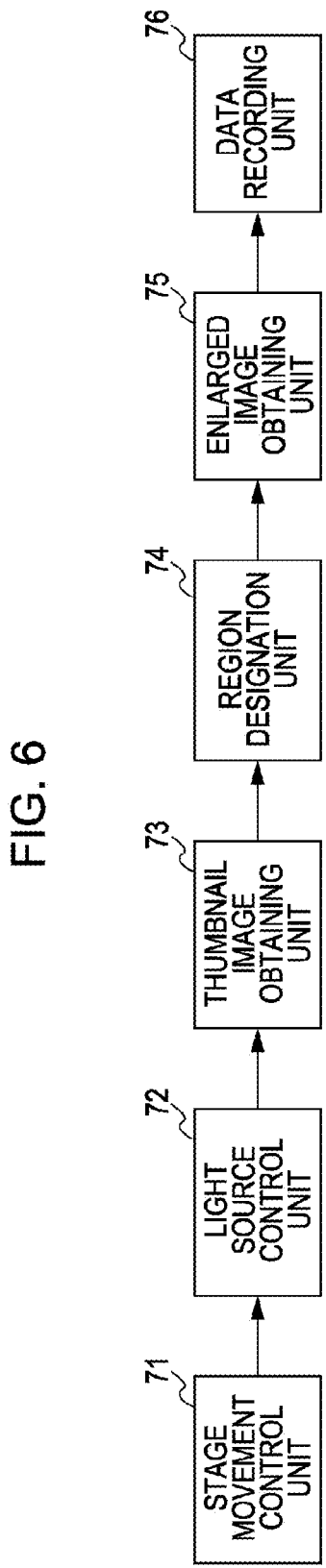
FIG. 6 is a block diagram illustrating a functional configuration of a CPU in a case of obtaining a biological sample image.

In accordance with the program corresponding to the command for obtaining an image of the biological sample SPL, the CPU 61 functions as a stage movement control unit 71, a light source control unit 72, a thumbnail image obtaining unit 73, a region designation unit 74, an enlarged image taking unit 75, and a data recording unit 76, as shown in FIG. 6.

The stage movement control unit 71 moves the movable stage 31 so that the slide glass SG is positioned at the thumbnail image taking position SGP.

For example, when the bright field mode is selected depending on the operation of the operation input unit 64, the light source control unit 72 drives the bright field illumination system 11 and the label illumination system 13 of the thumbnail image taking unit 10 so as to perform the bright field irradiation.

The thumbnail image obtaining unit 73 takes a bright field thumbnail image by using the thumbnail camera 14 and obtains it as the bright field thumbnail image data.

The region designation unit 74 performs a profile extraction processing where a profile of the biological sample SPL is extracted from the bright field thumbnail image data obtained by the thumbnail image obtaining unit 73. This profile extraction processing includes, for example, a binary processing for differentiating the biological sample SPL with other regions, and an outer shape extraction processing for extracting an outer shape of the biological sample SPL where the binary processing is performed.

Figure 7:
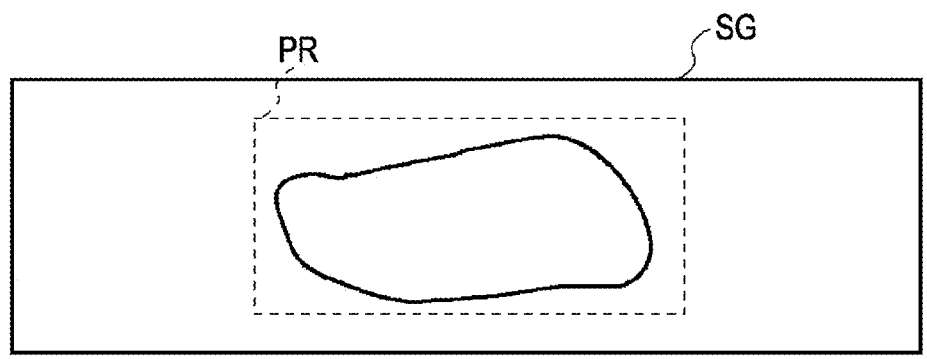
FIG. 7 is an outlined line diagram illustrating imaging regions included in the biological sample.

The region designation unit 74, as shown in FIG. 7, designates a sample region PR with a square shape, which includes the biological sample SPL obtained by the profile extraction processing and has a minimum area.

Successively, the stage movement control unit 71 moves the movable stage 31 so that the slide glass SG is positioned at the enlarged image taking position EGP. The light source control unit 72 drives the white light source 21 of the enlarged image taking unit 20.

Figure 8:
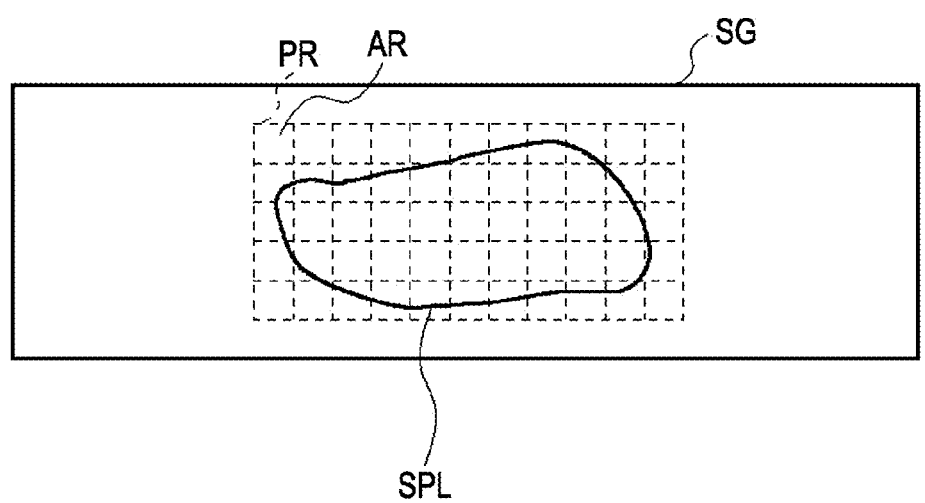
FIG. 8 is an outlined line diagram illustrating obtaining an image for each region in the biological sample.

The enlarged image obtaining unit 75, as shown in FIG. 8, divides the sample region PR designated by the region designation unit 74 into a plurality of imaging regions AR in accordance with the magnifications of the object lens 24 and the imaging lens 25 of the enlarged image taking unit 20. Also, in FIG. 8, the imaging regions AR do not overlap each other, but portions of adjacent regions may overlap each other.

The enlarged image obtaining unit 75 sequentially moves the movable stage 31 so that parts imaged by the imaging element 26 become the imaging regions AR, enables the imaging element 26 to image the parts, and thereby generates the bright field enlarged image by connecting images of the respective obtained parts to each other.

The data recording unit 76 generates bright field enlarged image data corresponding to the bright field enlarged image generated by the enlarged image obtaining unit 75, and records it in the storage unit 67.

The data recording unit 76 reads the attendant information from the label LB which is lighted to the bright field thumbnail image data obtained by the thumbnail image obtaining unit 73, associates the read information with the bright field enlarged image data, and records it in the storage unit 67.

In the meantime, for example, when the dark field mode is selected depending on the operation of the operation input unit 64, the stage movement control unit 71 moves the movable stage 31 so that the slide glass SG is positioned at the thumbnail image taking position SGP. The light source control unit 72 drives the dark field illumination system 12 of the thumbnail image taking unit 10 so as to perform the dark field irradiation.

The thumbnail image obtaining unit 73 takes a dark field thumbnail image by using the thumbnail camera 14 and obtains it as the dark field thumbnail image data.

The region designation unit 74 performs a profile extraction processing for the dark field thumbnail image data obtained by the thumbnail image obtaining unit 73, and designates a sample region PR with a square shape, which includes the biological sample SPL obtained by the processing and has a minimum area.

Successively, the stage movement control unit 71 moves the movable stage 31 so that the slide glass SG is positioned at the enlarged image taking position EGP. The light source control unit 72 drives the excitation light source 27 of the enlarged image taking unit 20.

The enlarged image obtaining unit 75 divides the sample region PR designated by the region designation unit 74 into a plurality of imaging regions AR. The enlarged image obtaining unit 75 sequentially moves the movable stage 31 so that parts imaged by the imaging element 26 become the imaging regions AR, enables the imaging element 26 to image the parts, and thereby generates the dark field enlarged image by connecting images of the respective obtained parts to each other.

The data recording unit 76 generates dark field enlarged image data corresponding to the dark field enlarged image generated by the enlarged image obtaining unit 75, and records it in the storage unit 67.

The data recording unit 76 associates the dark field thumbnail image data obtained by the thumbnail image obtaining unit 73 with the dark field enlarged image data, and records it in the storage unit 67. When the bright field enlarged image data corresponding to the dark field enlarged image data is stored in the storage unit 67, the data recording unit 76 associates the dark field enlarged image data with the bright field enlarged image data.

1-5. Operation and Effect

The biological sample image obtaining device 1 with the above-described configuration emits the excitation light from the excitation light source 51 so that, in the dark field mode, the fluorescent material (probe) marked on the target in the biological sample SPL lies in the non-excited state and the fluorescent material (DAPI) marked on the control with the probe lies in the excited state.

In addition, the biological sample image obtaining device 1 takes the image of the entire slide glass SG including the biological sample SPL as the dark field thumbnail image by using the thumbnail camera 14, in the state where the excitation light is emitted from the excitation light source 51.

Thereby, the biological sample image obtaining device 1 obtains the dark field thumbnail image (FIG. 4) where the fluorescent material in the biological sample SPL part emits fluorescence. Thus, the biological sample image obtaining device 1 can obtain the dark field thumbnail image where the outer shape of the fluorescently stained biological sample SPL which is transparent can be clearly recognized in the non-excited state.

At this time, the biological sample image obtaining device 1 excites only the fluorescent material (DAPI) marked on the control with the target but does not excite the fluorescent material (probe) marked on the target, and thereby it is possible to prevent the discoloration of the fluorescent material.

The fluorescent material (DAPI) marked on the control with the target is strong in the discoloration as compared with the fluorescent material (probe) marked on the target. Therefore, at the time of obtaining the dark field thumbnail image, even when the biological sample image obtaining device 1 excites the fluorescent material (DAPI) marked on the control with the target, the discoloration of the fluorescent material hardly occurs.

For this reason, the biological sample image obtaining device 1 can obtain the dark field thumbnail image with no discoloration of the fluorescent material (probe) marked on the target and with little discoloration of the fluorescent material (DAPI) marked on the control with the target.

Therefore, the biological sample image obtaining device 1 can obtain the dark field thumbnail image including the entirety of the fluorescently stained biological sample SPL without deterioration in the image quality.

Also, the biological sample image obtaining device 1 performs the profile extraction processing for the dark field thumbnail image data, and designates the sample region PR with a square shape, which includes the biological sample SPL obtained by the processing and has a minimum area.

The biological sample image obtaining device 1 takes the dark field enlarged image of the sample region PR designated regarding the dark field thumbnail image data. Thereby, the biological sample image obtaining device 1 can obtain the dark field enlarged image where the biological sample SPL is entirely included and a region not including the biological sample SPL is minimal, and thus it is possible to greatly reduce an amount of data.

Figure 9:
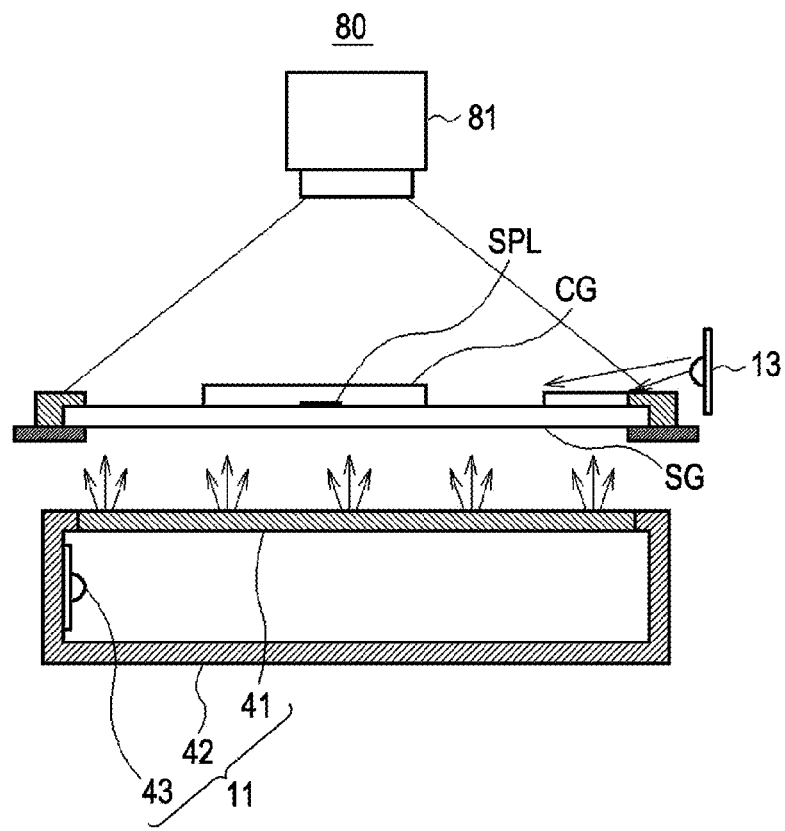
FIG. 9 is a diagram schematically illustrating a configuration of a bright field thumbnail image taking unit.
Figure 10:
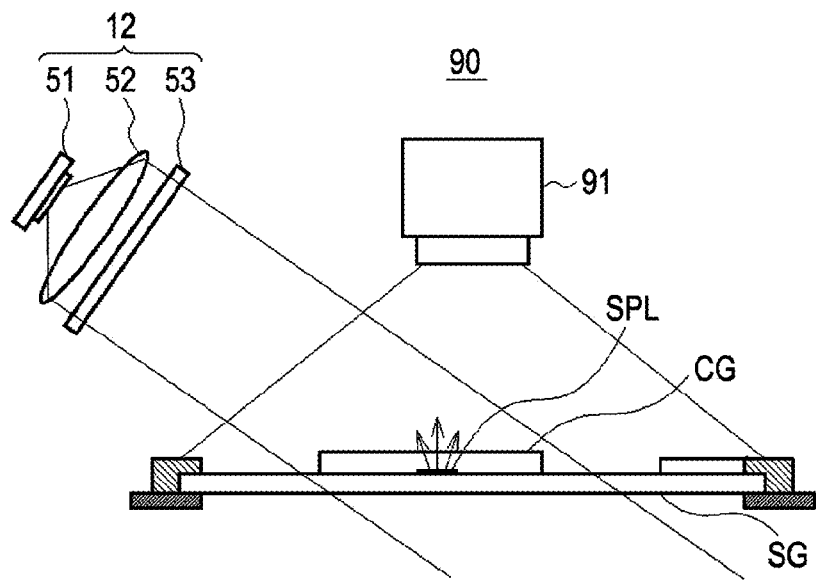
FIG. 10 is a diagram schematically illustrating a configuration of a dark field thumbnail image taking unit.

The biological sample image obtaining device 1 may employ a bright field thumbnail image taking unit 80 and a dark field thumbnail image taking unit 90 instead of the thumbnail image taking unit 10, as shown in FIGS. 9 and 10 where the same reference numerals are given to the corresponding parts in FIG. 2.

The bright field thumbnail image taking unit 80 and the dark field thumbnail image taking unit 90 are respectively provided with thumbnail cameras 81 and 91 different from each other and are arranged at predetermined positions different from each other in the microscope 2. The bright field 80 and the dark field thumbnail image taking unit 90 respectively take a bright field thumbnail image and a dark field thumbnail image when the slide glass SG is moved to each of predetermined imaging positions by the movable stage 31.

However, in the configuration of employing the bright field thumbnail image taking unit 80 and the dark field thumbnail image taking unit 90, the microscope 2 becomes large since they are disposed at predetermined positions different from each other. In addition, since the thumbnail cameras 81 and 91 are respectively provided, the structure thereof is complicated in addition to an increase in the number of components.

Figure 11:
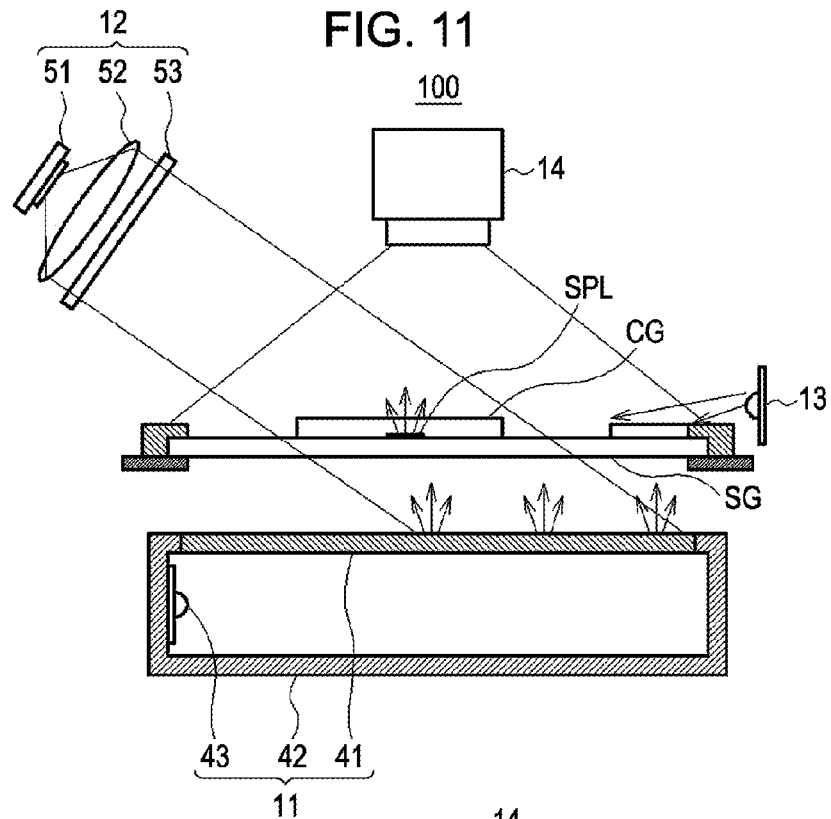
FIG. 11 is a diagram schematically illustrating a configuration of a thumbnail image taking unit formed by combining the bright field thumbnail image taking unit and the dark field thumbnail image taking unit.

Thus, a thumbnail image taking unit 100 configured by simply combining the bright field thumbnail image taking unit 80 with the dark field thumbnail image taking unit 90 is considered and shown in FIG. 11. This thumbnail image taking unit 100 is provided such that the excitation light emitted from the excitation light source 51 reaches the imaging range of the thumbnail camera 14 in the diffusion plate 41.

In the thumbnail image taking unit 100, in the dark field mode, the excitation light emitted from the excitation light source 51 is irradiated to the diffusion plate 41, and the excitation light diffused by the diffusion plate 41 is irradiated toward the thumbnail camera 14.

When the thumbnail camera 14 takes a dark field thumbnail image in the dark field mode, since the dark field thumbnail image contains the excitation light diffused by the diffusion plate 41, it causes the image quality of the dark field thumbnail image to be deteriorated.

In addition, for example, when the diffusion plate 41 is made of, for example, organic material such as milky acryl material or the like, the diffusion plate 41 may be excited by the excitation light to emit fluorescence. In this case as well, the image quality of the dark field thumbnail image is deteriorated.

In contrast, in the thumbnail image taking unit 10 according to an embodiment of the application, the excitation light source 51 irradiates the excitation light to the biological sample SPL with a tilted angle larger than about a half of the angle of view θ of the thumbnail camera 14 with respect to the optical axis of the thumbnail camera 14. In addition, the excitation light source 51 irradiates the excitation light to a range exceeding the imaging range of the thumbnail camera 14 in the diffusion plate 41.

Therefore, in the biological sample image obtaining device 1 in the dark field mode, even when the excitation light emitted from the excitation light source 51 is diffused by the diffusion plate 41, the excitation light does not reach the imaging range of the thumbnail camera 14, and thereby the image quality of the dark field thumbnail image is not deteriorated.

According to the above-described configuration, the excitation light is emitted from the excitation light source 51 such that the fluorescent material marked on the target in the biological sample SPL lies in the non-excited state and the fluorescent material marked on the control with the target lies in the excited state, and thereby the image of the entire slide glass SG where the biological sample SPL is disposed is taken as the dark field thumbnail image by the thumbnail camera 14.

Thereby, the biological sample image obtaining device 1 can obtain the dark field thumbnail image (FIG. 4) including the entirety of the fluorescently stained biological sample SPL without deterioration in the image quality.

1-6. Other Embodiments

Although there has been described the case where the bright field illumination system 11 and the dark field illumination system 12 is provided in the thumbnail image taking unit 10 in the above-described embodiment, the present application is not limited thereto, but only the dark field illumination system 12 may be provided.

Although, in the above-described embodiment, there has been described the case where the thumbnail image taking unit 10 is employed as a part for taking the thumbnail image in the biological sample image obtaining device 1, the thumbnail image taking unit is not limited thereto.

Figure 12:
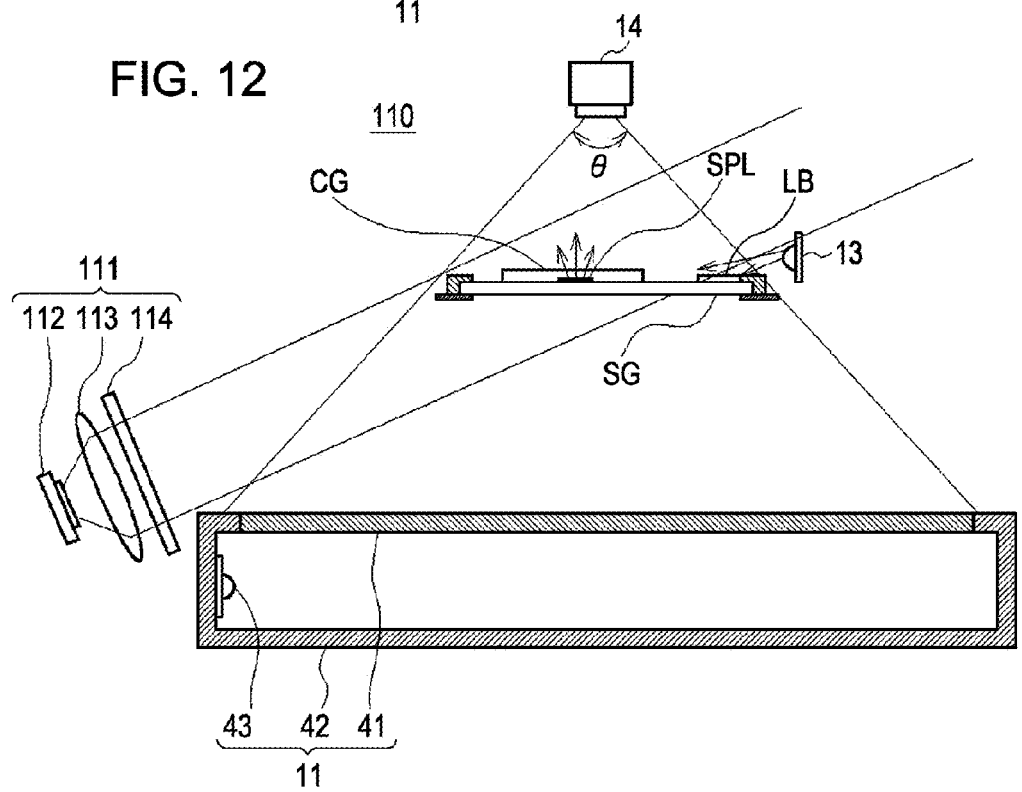
FIG. 12 is a diagram schematically illustrating a configuration of a thumbnail image taking unit (1) according to another embodiment.

For example, as shown in FIG. 12 where the same reference numerals are given to the corresponding parts in FIG. 2, a thumbnail image taking unit 110 may be employed instead of the thumbnail image taking unit 10.

In the thumbnail image taking unit 110 like the thumbnail image taking unit 10, the bright field illumination system 11 is provided at an opposite side to the thumbnail camera 14 with the slide glass SG interposed therebetween. In addition, in the thumbnail image taking unit 110, the label illumination system 13 is provided at the same surface side of the slide glass SG as the thumbnail camera 14.

Meanwhile, in the thumbnail image taking unit 110, a dark field illumination system 111 is provided at an opposite side to the thumbnail camera 14 with respect to the slide glass SG. That is to say, the dark field illumination system 111 and the bright field illumination system 11 are provided at the same surface side of the slide glass SG.

An excitation light source 112 irradiates, in the dark field mode, the light with the wavelength of about 365 nm to the region where the biological sample SPL is disposed, with a tilted angle larger than about a half of the angle of view θ of the thumbnail camera 14 with respect to the optical axis of the thumbnail camera 14. In addition, the excitation light source 112 is provided at a position where an emitted light is not directly irradiated to the imaging area of the thumbnail camera 14.

The light emitted from the excitation light source 112 is converted into a parallel light by a condenser 113 and is irradiated to the biological sample SPL as the excitation light via an excitation filter 114.

The thumbnail camera 14 images the entire slide glass SG including the biological sample SPL. At this time, the excitation light emitted from the excitation light source 112 is not irradiated to the diffusion plate 41 or the imaging area of the thumbnail camera 14. Therefore, the thumbnail image taking unit 110 can take the dark field thumbnail image without deterioration in the image quality.

Figure 13:
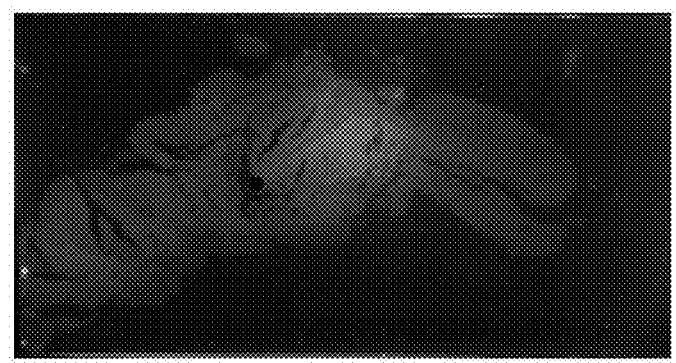
FIG. 13 is a diagram illustrating a bright field thumbnail image taken by the thumbnail image taking unit (1) according to another embodiment.

Here, FIG. 13 shows as an example a region part where the biological sample SPL in the dark field thumbnail image is disposed in the case where the biological sample SPL is stained by PathVysion of the HER-2DNA probe kit and DAPI as the fluorescent stain.

In this way, like the thumbnail image taking unit 10, the thumbnail image taking unit 110 can take the dark field thumbnail image where the outer shape of the DAPI stained biological sample SPL can be clearly recognized.

Figure 14:
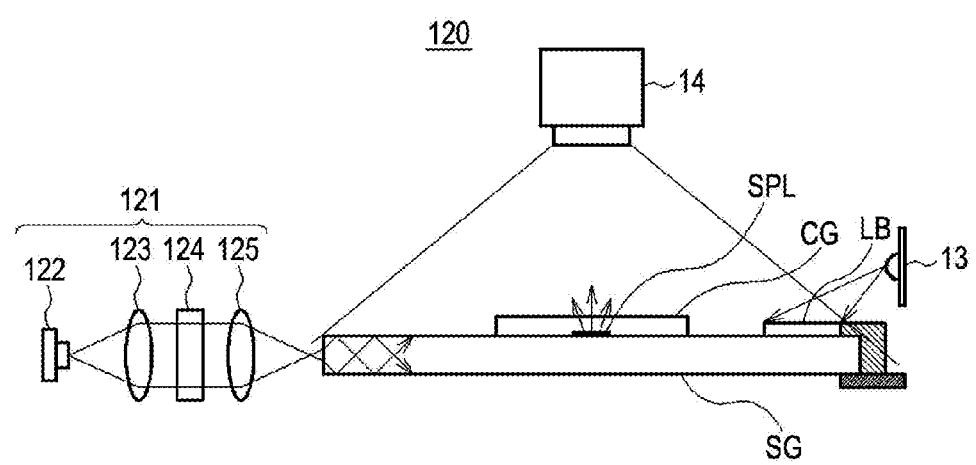
FIG. 14 is a diagram schematically illustrating a configuration of a thumbnail image taking unit (2) according to another embodiment.

As another example, as shown in FIG. 14 where the same reference numerals are given to the corresponding parts in FIG. 2, a thumbnail image taking unit 120 may be employed instead of the thumbnail image taking unit 10. In relation thereto, the bright field illumination system 11 is omitted for convenience.

Like the thumbnail image taking unit 10, in the thumbnail image taking unit 120, the bright field illumination system 11 is provided at an opposite side to the thumbnail camera 14 with the slide glass SG interposed therebetween. Also, in the thumbnail image taking unit 120, the label illumination system 13 is provided at the same surface side of the slide glass SG as the thumbnail camera 14.

Meanwhile, in the thumbnail image taking unit 120, a dark field illumination system 121 is provided at the lateral surface side of the slide glass SG.

An excitation light source 122 emits light with the wavelength of about 365 nm to the lateral surface of the slide glass SG. The light emitted from the excitation light source 122 is converted into a parallel light by a condenser 123, condensed by a condenser 125 via an excitation filter 124, and is incident inside the slide glass SG from the lateral surface of the slide glass SG.

The light incident inside the slide glass SG repeats reflection from the top and the bottom of the slide glass SG to be guided inward and then is irradiated to the biological sample SPL as the excitation light.

The thumbnail camera 14 images the entire slide glass SG including the biological sample SPL. At this time, the exci-
tation light emitted from the excitation light source 122 is not irradiated to the diffusion plate 41 or the imaging area of the thumbnail camera 14. Therefore, the thumbnail image taking unit 120 can take the dark field thumbnail image without deterioration in the image quality.

Figure 15:
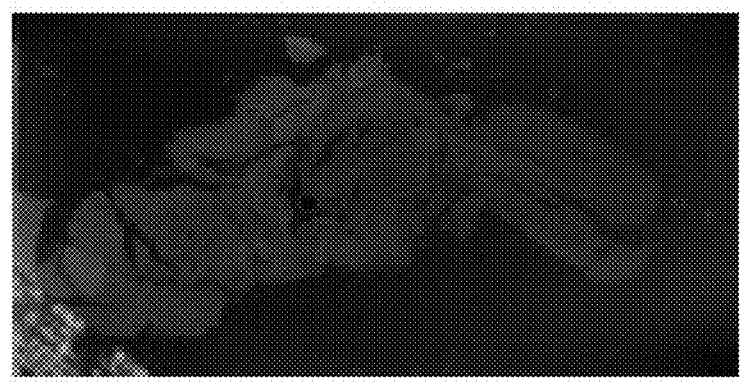
FIG. 15 is a diagram illustrating a bright field thumbnail image taken by the thumbnail image taking unit (2) according to another embodiment.

Here, FIG. 15 shows as an example a region part where the biological sample SPL in the dark field thumbnail image is disposed in the case where the biological sample SPL is stained by PathVysion of the HER-2DNA probe kit and DAPI as the fluorescent stain.

In this way, like the thumbnail image taking unit 10 and 110, the thumbnail image taking unit 120 can take the dark field thumbnail image where the outer shape of the DAPI stained biological sample SPL can be clearly recognized.

In relation thereto, when the thumbnail image taking unit 120 is employed, the light emitted from the excitation light source 122 is guided to the slide glass SG by making open, for example, a portion of the slide holder 32 and the slide pressure 33 in the dark field illumination system 121 side.

Figure 16:
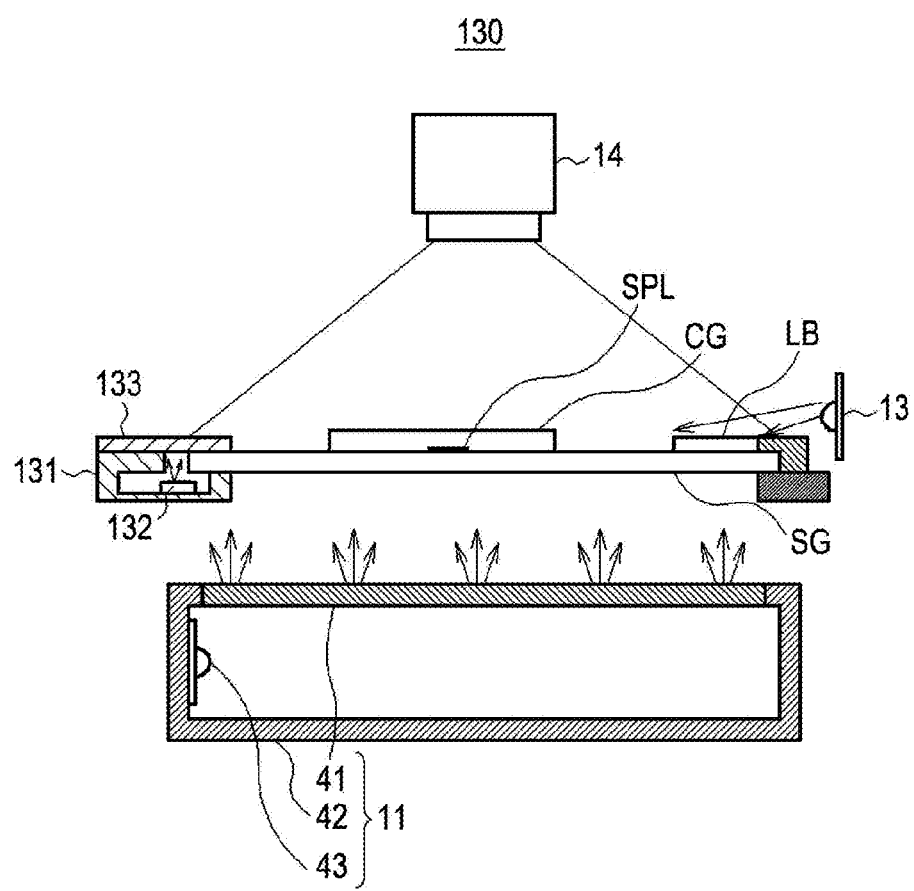
FIG. 16 is a diagram schematically illustrating a configuration of a thumbnail image taking unit (3) according to another embodiment.

As another example, as shown in FIG. 16 where the same reference numerals are given to the corresponding parts in FIG. 2, a thumbnail image taking unit 130 may be employed instead of the thumbnail image taking unit 10 and the slide holder 32.

Like the thumbnail image taking unit 10, in the thumbnail image taking unit 130, the bright field illumination system 11 is provided at an opposite side to the thumbnail camera 14 with the slide glass SG interposed therebetween. Also, in the thumbnail image taking unit 130, the label illumination system 13 is provided at the same surface side of the slide glass SG as the thumbnail camera 14.

Figure 17A:
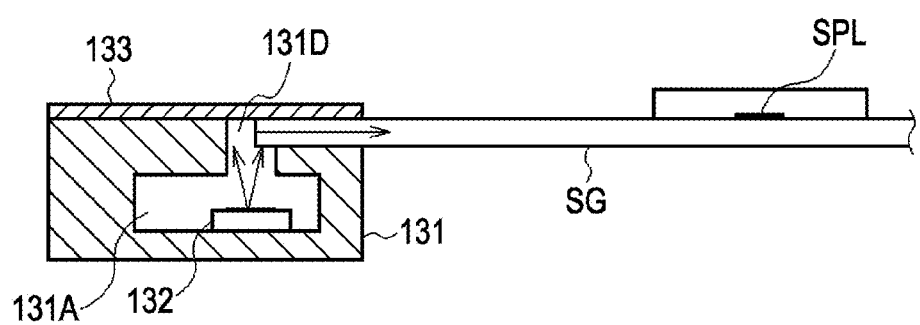
FIGS. 17A and 17B are diagrams schematically illustrating a configuration of a dark field illumination system of the thumbnail image taking unit (3) according to another embodiment.
Figure 17B:
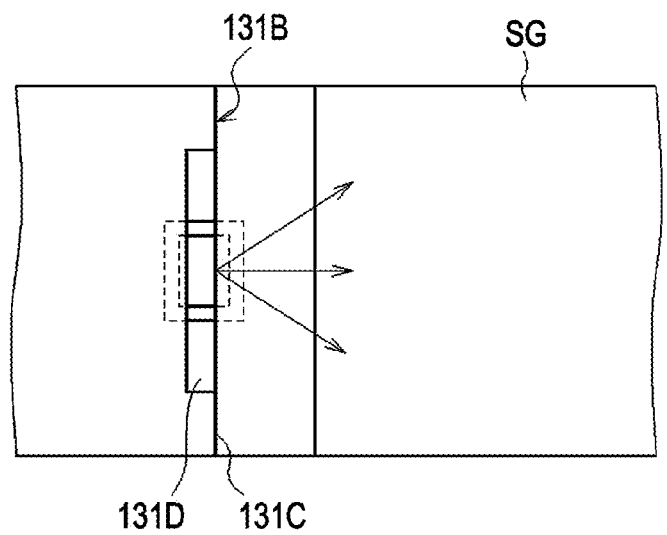

Meanwhile, as shown in FIGS. 17A and 17B in detail, in the thumbnail image taking unit 130, a space 131A of which lateral surfaces are made of high reflective metal is formed in the slide holder 131 at one end of the slide glass SG. In the slide holder 131, an upper portion of the space 131A is open in a rectangle shape.

In addition, in the thumbnail image taking unit 130, an excitation light source 132 constituted by an LED of which one side is about 6 mm is provided in the space 131A of the slide holder 131.

In the slide holder 131, when the slide glass SG is disposed, the slide glass SG has contact with the slide glass contact surfaces 131B and 131C to be fixed. At this time, a cube shaped space 131D with a width of 2 mm is formed between the slide holder 131 and the slide glass SG.

When the slide glass SG is fixed to the slide holder 131, the slide pressure 133 is disposed to cover the slide holder 131 and one end of the slide glass SG. The slide pressure 133 is formed of, for example, black aluminum anodized film and prevents reflection of light.

The excitation light source 132 emits light with the wavelength of about 365 nm to the lateral surface of the slide glass SG in the dark field mode. The light emitted from the excitation light source 132 is incident inside the slide glass SG from the lateral surface of the slide glass SG directly or after reflected from the lateral surfaces of the spaces 131A and 131D.

The light incident inside the slide glass SG repeats reflection from the top and bottom of the slide glass SG to be guided inward, and is irradiated to the biological sample SPL as the excitation light.

The thumbnail camera 14 images the entire slide glass SG including the biological sample SPL. At this time, the excitation light emitted from the excitation light source 132 is not irradiated to the diffusion plate 41 or the imaging area of the thumbnail camera 14. Therefore, the thumbnail image taking unit 130 can take the dark field thumbnail image without deterioration in the image quality.

In this way, like the thumbnail image taking units 10, 110 and 120, the thumbnail image taking unit 130 can take the dark field thumbnail image where the outer shape of the DAPI stained biological sample SPL can be clearly recognized.

In addition, the thumbnail image taking unit 130 can downsize the entire device by forming the excitation light source 132 in the slide holder 131 as compared with the thumbnail image taking units 10, 110 and 120 where the dark field illumination system 121 is formed independently from the slider holder 32.

Figure 18:
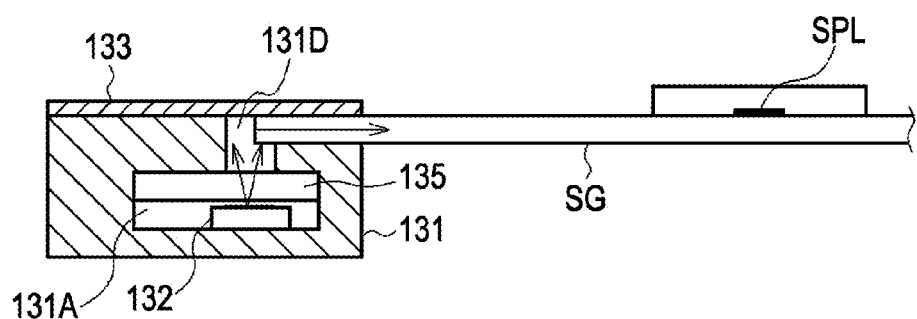
FIG. 18 is a diagram schematically illustrating a configuration of a dark field illumination system according to another embodiment.

In the thumbnail image taking unit 130, as shown in FIG. 18 where the same reference numerals are given to the corresponding parts in FIG. 17, an emission filter 135, which restricts a wavelength range of the light emitted from the excitation light source 132 in the space 131A, may be disposed at the light emission side of the excitation light source 132.

Although there has been described the case where nothing is present between the thumbnail camera 14 and the slide glass SG in the above-described embodiment, the present application is not limited thereto, but an emission filter for cutting light with the wavelength of 365 nm may be disposed therebetween.

In addition, in the above-described embodiment, there has been described the case where PathVysion of HER-2DNA probe kit made by Abbott Corporation, which performs hybridization for the gene HER2/neu and the alpha satellite DNA sequence inside the cell nucleus, is employed as the fluorescent material marked on the target. The present application is not limited thereto, but fluorescent materials which mark specific genes, cells or the like in the biological sample SPL are also possible.

In the above-described embodiment, there has been described the case where DAPI is employed as the fluorescent material marked on the control with the target. The present application is not limited thereto, but fluorescent materials which enable an outer shape of the biological sample SPL to be found are also possible.

In addition, in the above-described embodiment, there has been described the case where the CPU 61 performs the above-described biological sample image obtaining processing in accordance with the programs stored in the ROM 62. The present application is not limited thereto, but the above-described biological sample image obtaining processing may be performed in accordance with programs which are installed from storage media or downloaded from the Internet. Also, the above-described biological sample image obtaining processing may be performed in accordance with programs which are installed by other various kinds of routes.

In the above-described embodiment, there has been described the case where the excitation light source 51 is provided as a light source and the thumbnail camera 14 is provided as an imaging unit. However, in the present application, light sources and imaging units having other various kinds of configurations may be provided.

2. Second Embodiment

In the second embodiment, obtaining the dark field thumbnail image will be described, and obtaining the bright field thumbnail image, the bright field enlarged image, and the dark field enlarged image is the same as that in the first embodiment, and thus the description thereof will be omitted.

When the dark field thumbnail image of the entire slide glass SG is taken by the biological sample image obtaining device 1 in the dark field mode in the first embodiment, the dark field thumbnail image is obtained by the excitation and light-emission of DAPI in the biological sample SPL part.

Figure 19:
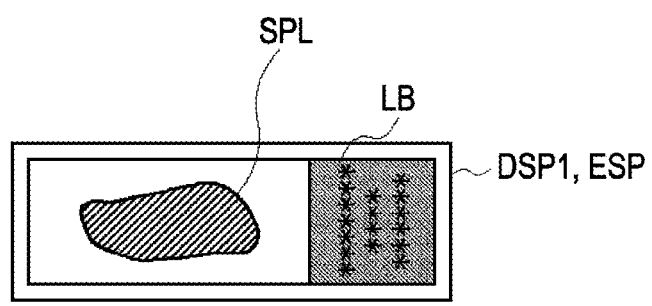
FIG. 19 is an outlined line diagram illustrating a dark field thumbnail image (1) according to a second embodiment.

Accordingly, in this case, a dark field thumbnail image DSP1 as shown in FIG. 19 is obtained, and, in the dark field thumbnail image DSP1, the outer shape of the fluorescently stained biological sample SPL is clearly recognized, but the written contents of the label LB fail to be recognized.

In the second embodiment, the outer shape of the fluorescently stained biological sample SPL can be recognized in the dark field thumbnail image. Also, the dark field thumbnail image where the written contents of the label LB can also be recognized is obtained.

2-1. Configuration of Thumbnail Image Taking Unit

Figure 20:
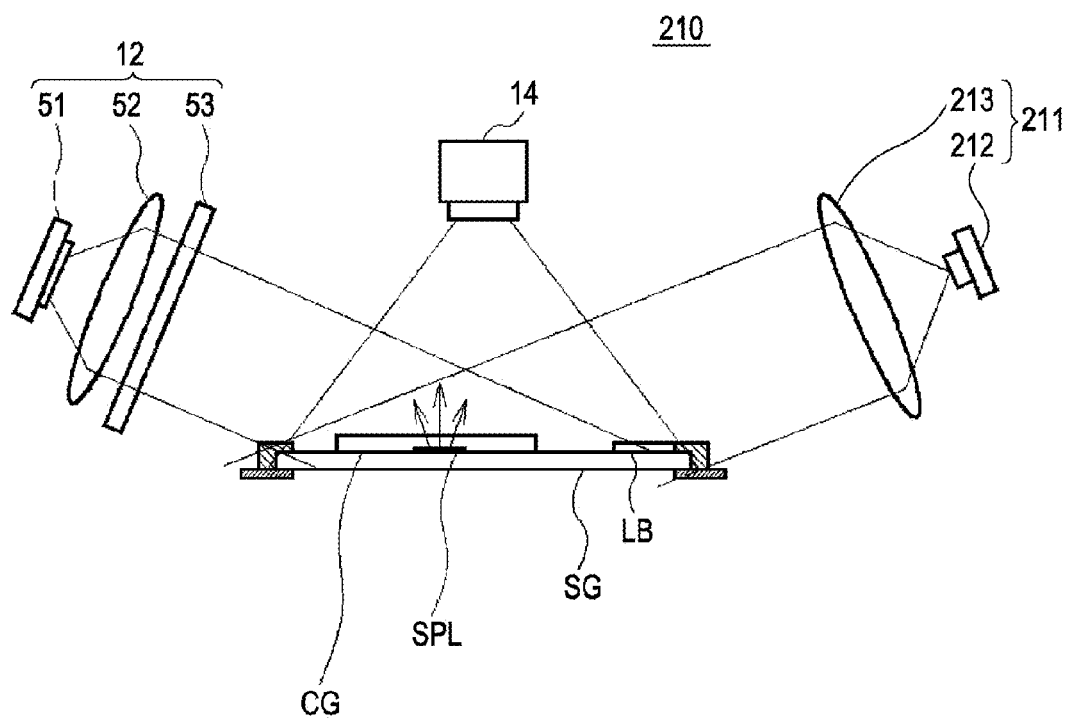
FIG. 20 is a diagram schematically illustrating a configuration of a thumbnail image taking unit according to the second embodiment.

In the second embodiment, there is a configuration of a biological sample image obtaining device 200 (FIG. 1) as a whole, and a thumbnail image taking unit 210 is provided instead of the thumbnail image taking unit 10 in the first embodiment as shown in FIG. 20 where the same reference numerals are given to the corresponding parts in FIG. 2. Here, a bright field illumination system is not shown in FIG. 20, but, for example, the bright field illumination system 11 in the thumbnail image taking unit 10 may be employed.

The thumbnail image taking unit 210 is provided with the dark field illumination system 12 which irradiates excitation light with a wavelength of exciting DAPI to a region where the biological sample SPL is disposed, and a white illumination system 211 which irradiates a white light to the entire slide glass SG, in the dark field mode. The thumbnail camera 14, the dark field illumination system 12, and the white illumination system 211 are provided at the same surface side of the slide glass SG.

The white illumination system 211 is constituted by a white LED 212 and a condenser 213, and a white light emitted from the white LED 212 is converted by the condenser 213 into a roughly parallel light which is irradiated to the entire slide glass SG.

2-2. Detailed Contents of Biological Sample Image Obtaining Processing

When receiving a command for obtaining an image of the biological sample SPL from the operation input unit 64, the CPU 61 (FIG. 5) develops a program corresponding to the command in the RAM 63.

The CPU 61 functions as the stage movement control unit 71, the light source control unit 72, the thumbnail image obtaining unit 73, the region designation unit 74, the enlarged image obtaining unit 75, and the data recording unit 76, in accordance with the program corresponding to the command for obtaining an image of the biological sample SPL, as shown in FIG. 6.

The light source control unit 72 drives the excitation light source 51 of the dark field illumination system 12 when the dark field mode is selected. The thumbnail image obtaining unit 73 images the entire slide glass SG by using the thumbnail camera 14 in the state where the excitation light emitted from the excitation light source 51 of the dark field illumination system 12 is irradiated, and obtains it as the excitation light thumbnail image ESP (FIG. 19).

Figure 21:
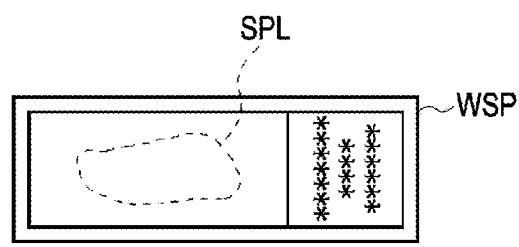
FIG. 21 is an outlined line diagram illustrating a white light thumbnail image.

In addition, the light source control unit 72 stops driving the excitation light source 51 and drives the white LED 212 of the white illumination system 211. The thumbnail image obtaining unit 73 images the entire slide glass SG by using the thumbnail camera 14 in the state where the white light emitted from the white LED 212 of the white illumination system 211 is being irradiated, and obtains it as a white light thumbnail image WSP as shown in FIG. 21. In addition, since the biological sample SPL is transparent in the bright field, an image thereof is not contained in the white light thumbnail image WSP, but, for convenience of description, the profile of the biological sample SPL indicated by the broken line is shown in FIG. 21.

In the excitation light thumbnail image ESP obtained in this way, the outer shape of the biological sample SPL can be clearly recognized, but the written contents of the label LB fail to be recognized. Meanwhile, in the white light thumbnail image WSP, the outer shape of the biological sample SPL fail to be recognized, but the written contents of the label LB can be recognized.

The thumbnail image obtaining unit 73 generates a dark field thumbnail image DSP2 where the obtained excitation light thumbnail image ESP and white light thumbnail image ESP are arranged, for example, in the longitudinal direction, as shown in FIG. 22, and stores it in the storage unit 67 as dark field thumbnail image data.

Thereby, in the dark field thumbnail image DSP2, the outer shape of the fluorescently stained biological sample SPL can be recognized from the excitation light thumbnail image ESP part which has been taken in the dark field. Along therewith, the written contents of the label LB can be recognized from the white light thumbnail image WSP part which has been taken in the bright field.

2-3. Operation and Effect

The biological sample image obtaining device 200 with the above-described configuration emits the excitation light from the excitation light source 51 so that the fluorescent material (probe) marked on the target in the biological sample SPL lies in the non-excited state and the fluorescent material (DAPI) marked on the control with the probe lies in the excited state.

The biological sample image obtaining device 200 images the entire slide glass SG including the biological sample SPL by using the thumbnail camera 14 in the state where the excitation light source 51 irradiates the excitation light to the entire slide glass SG, and obtains it as the excitation light thumbnail image ESP.

In addition, the biological sample image obtaining device 200 irradiates, using the white LED 212, the white light to the entire slide glass SG including the label LB which is disposed at one end of the slide glass SG and is a region containing attendant information for the biological sample SPL.

The biological sample image obtaining device 200 images, using the thumbnail camera 14, the entire slide glass SG including the label LB in the state where the white light from the white LED 212 is irradiated to the entire slide glass SG, and obtains it as the white light thumbnail image WSP.

The biological sample image obtaining device 200 generates the dark field thumbnail image constituted by at least the region part where the biological sample SPL is disposed in the excitation light thumbnail image ESP and at least the label LB part in the white light thumbnail image WSP.

Thereby, in the biological sample image obtaining device 200, the outer shape of the fluorescently stained biological sample SPL can be recognized from the excitation light thumbnail image ESP. Also, the written contents of the label LB can be recognized from the white light thumbnail image WSP which is taken in the bright field.

Further, the biological sample image obtaining device 200 obtains an image of the entire slide glass SG including the label LB as the white light thumbnail image WSP in the state where the white light is being irradiated from the white LED 212. Thereby, the biological sample image obtaining device 200 can also record marks or symbols or the like written on the slide glass SG with an oil pen, etc., by a doctor or the like, and thus when the dark field thumbnail images are searched by the doctor or the like, they can be easily identified by the marks or the symbols.

According to the above-described configuration, the excitation light is emitted from the excitation light source 51 such that the fluorescent material marked on the target lies in the non-excited state and the fluorescent material marked on the control with the target lies in the excited state, and thereby the image of the entire slide glass SG including the biological sample SPL is obtained.

In addition, the image of the entire slide glass SG including the label LB is obtained by irradiating the white light from the white LED 212 to the entire slide glass SG including the label LB which is disposed at one end of the slide glass SG and is a region containing attendant information for the biological sample SPL.

Thereby, the biological sample image obtaining device 200 can obtain the dark field thumbnail image where the outer shape of the biological sample SPL can be recognized and the written contents of the label LB can also be recognized.

2-4. Other Embodiments

In the second embodiment described above, there has been described the case where the dark field thumbnail image DSP2 is generated by combining the excitation light thumbnail image ESP which has been taken in the dark field with the white light thumbnail image WSP which has been taken in the bright field. The present application is not limited thereto.

For example, the thumbnail image obtaining unit 73 obtains the excitation light thumbnail image ESP in the state where the excitation light source 51 is driven by the light source control unit 72, as shown in FIG. 23A. Also, the thumbnail image obtaining unit 73 obtains the white light thumbnail image WSP in the state where the white LED 212 is driven by the light source control unit 72, as shown in FIG. 23B.

The thumbnail image obtaining unit 73 extracts the part other than the label LB of the slide glass SG from the obtained excitation light thumbnail image ESP. That is to say, the thumbnail image obtaining unit 73 extracts the part where the biological sample SPL is disposed from the excitation light thumbnail image ESP.

In addition, the thumbnail image obtaining unit 73 extracts the label LB part of the slide glass SG from the obtained white light thumbnail image WSP.

The thumbnail image obtaining unit 73 generates the dark field thumbnail image DSP3 by combining the part other than the label LB of the slide glass SG extracted from the excitation light thumbnail image ESP with the label LB part of the slide glass SG extracted from the white light thumbnail image WSP.

Thereby, the biological sample image obtaining device 200 can obtain the dark field thumbnail image DSP3 where the outer shape of the fluorescently stained biological sample SPL can be recognized and the written contents of the label LB can also be recognized.

Figure 24A:
FIGS. 24A to 24C are outlined line diagrams illustrating dark field thumbnail images (4) according to the second embodiment.

As another example, the thumbnail image obtaining unit 73 obtains an excitation light thumbnail image ESP in the state where the excitation light source 51 is driven, and performs a profile extraction processing for extracting a profile of the biological sample SPL for the excitation light thumbnail image ESP. In addition, the thumbnail image obtaining unit 73 generates a profile image SDP where a profile of the biological sample SPL is extracted, as shown in FIG. 24A.

Figure 24B:
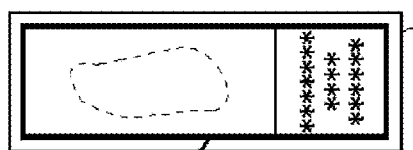

Further, the thumbnail image obtaining unit 73 obtains a white light thumbnail image WSP in the state where the white LED 212 is driven, as shown in FIG. 24B.

Figure 24C:
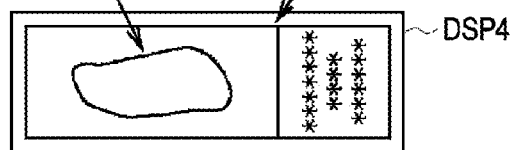

The thumbnail image obtaining unit 73 generates a dark field thumbnail image DSP4 where information for the profile of the biological sample SPL in the profile image SDP is synthesized with the white light thumbnail image WSP, as shown in FIG. 24C.

In this case as well, the biological sample image obtaining device 200 can generate the dark field thumbnail image DSP4 where the outer shape of the fluorescently stained biological sample SPL can be recognized and the written contents of the label LB can also be recognized. In addition, the biological sample image obtaining device 200 can record marks or symbols or the like written in the slide glass SG with an oil pen, etc., by a doctor or the like, in the dark field thumbnail image DSP4.

As another example, the thumbnail image obtaining unit 73 obtains the excitation light thumbnail image ESP in the state where the excitation light source 51 is driven, and generates the profile image SDP (FIG. 24A) by performing the profile extraction processing for the excitation light thumbnail image ESP. The thumbnail image obtaining unit 73 obtains the white light thumbnail image WSP (FIG. 24B) in the state where the white LED 212 is driven.

Figure 25:
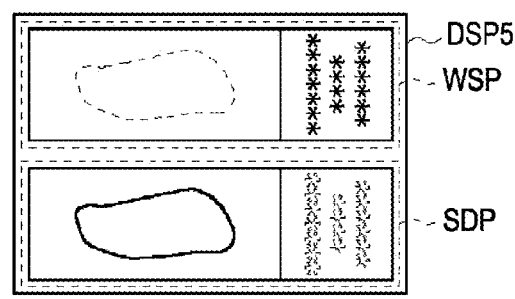
FIG. 25 is an outlined line diagram illustrating a dark field thumbnail image (5) according to a second embodiment.

The thumbnail image obtaining unit 73 generates a dark field thumbnail image DSP5 where the white light thumbnail image WSP and the profile image SDP are arranged, for example, in the longitudinal direction, as shown in FIG. 25.

In this case as well, the biological sample image obtaining device 200 can generate the dark field thumbnail image DSP5 where the outer shape of the fluorescently stained biological sample SPL can be recognized and the written contents of the label LB can also be recognized. In addition, the biological sample image obtaining device 200 can record marks or symbols or the like written in the slide glass SG with an oil pen, etc., by a doctor or the like, in the dark field thumbnail image DSP5.

In the second embodiment described above, there has been described the case where the biological sample image obtaining device 200 is provided with thumbnail image taking unit 210. The present application is not limited thereto.

Figure 26:
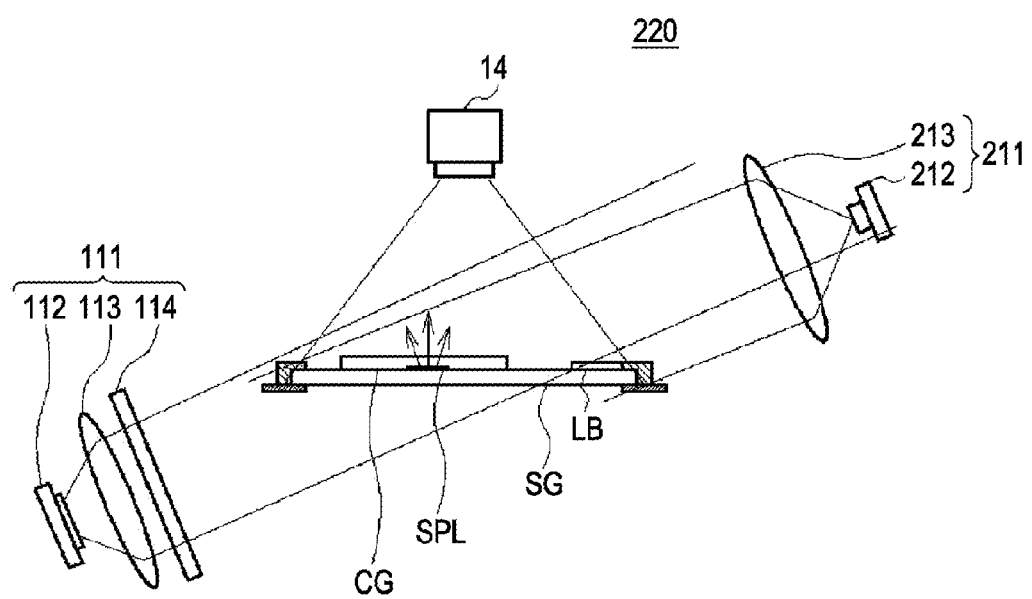
FIG. 26 is a diagram schematically illustrating a configuration of a dark field illumination system of a thumbnail image taking unit (4) according to another embodiment.

For example, as shown in FIG. 26 where the same reference numerals are given to corresponding parts in FIGS. 12 and 20, a thumbnail image taking unit 220 may be employed instead of the thumbnail image taking unit 210.

In the thumbnail image taking unit 220, the dark field illumination system 111 is provided at an opposite side to the thumbnail camera 14 with the slide glass SG interposed therebetween, and the white illumination system 211 is provided at the same surface side of the slide glass SG as the thumbnail camera 14.

Figure 27:
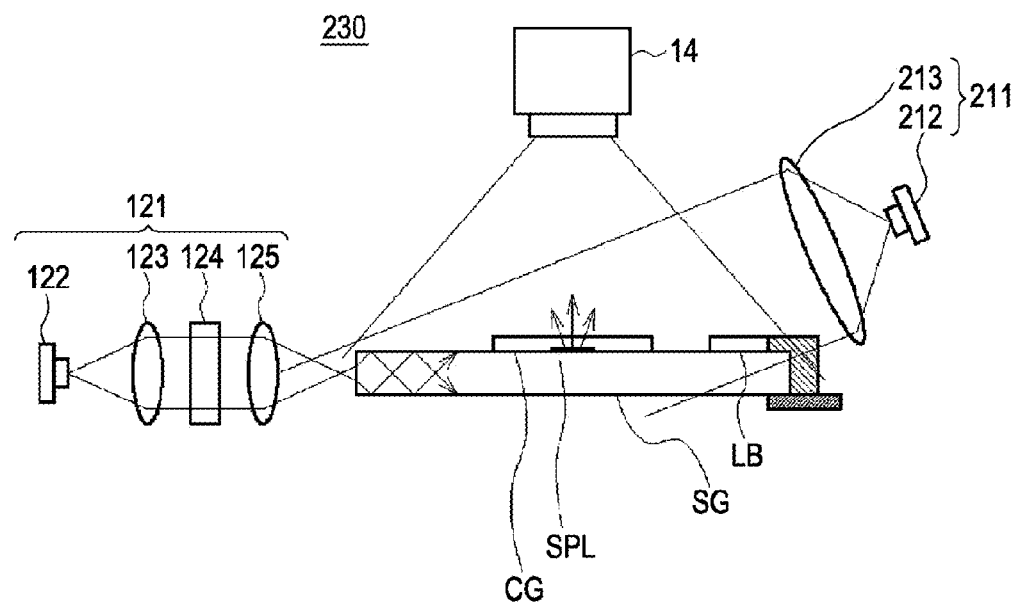
FIG. 27 is a diagram schematically illustrating a configuration of a dark field illumination system of a thumbnail image taking unit (5) according to another embodiment.

As another example, as shown in FIG. 27 where the same reference numerals are given to the corresponding parts in FIGS. 14 and 20, a thumbnail image taking unit 230 may be employed instead of the thumbnail image taking unit 210.

In the thumbnail image taking unit 230, the dark field illumination system 121 is provided at a lateral surface side of the slide glass SG, and the white illumination system 211 is provided at the same surface side of the slide glass SG as the thumbnail camera 14.

The light emitted from the excitation light source 122 is converted into a parallel light by the condenser 123, condensed by the condenser 125 via the excitation filter 124, and is incident inside the slide glass SG from the lateral surface of the slide glass SG. The light incident inside the slide glass SG repeats reflection from the top and the bottom of the slide glass SG to be guided inward and then is irradiated to the biological sample SPL as the excitation light.

Figure 28:
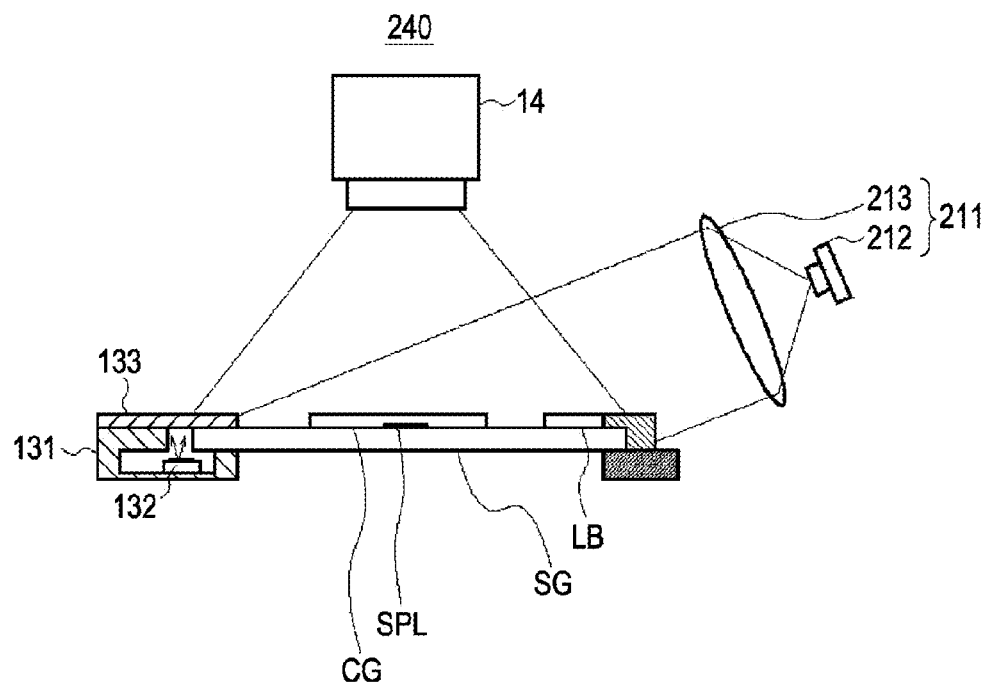
FIG. 28 is a diagram schematically illustrating a configuration of a dark field illumination system of a thumbnail image taking unit (6) according to another embodiment.

As another example, as shown in FIG. 28 where the same reference numerals are given to the corresponding parts in FIGS. 16 and 20, a thumbnail image taking unit 240 may be employed instead of the thumbnail image taking unit 210.

In the thumbnail image taking unit 240, the white illumination system 201 is provided at an opposite side to the thumbnail camera 14 with the slide glass SG interposed therebetween, and an excitation light source 132 is provided in the slide holder 131.

The light emitted from the excitation light source 132 is incident inside the slide glass SG from the lateral surface of the slide glass SG, repeats reflection from the top and the bottom of the slide glass SG to be guided inward and then is irradiated to the biological sample SPL as the excitation light.

Like the thumbnail image taking unit 210, these thumbnail image taking units 220, 230 and 240 can obtain the dark field thumbnail images DSP2, DSP3, DSP4 and DSP5.

For convenience of description, the bright field illumination system is omitted in the thumbnail image taking units 220, 230 and 240.

Figure 29:
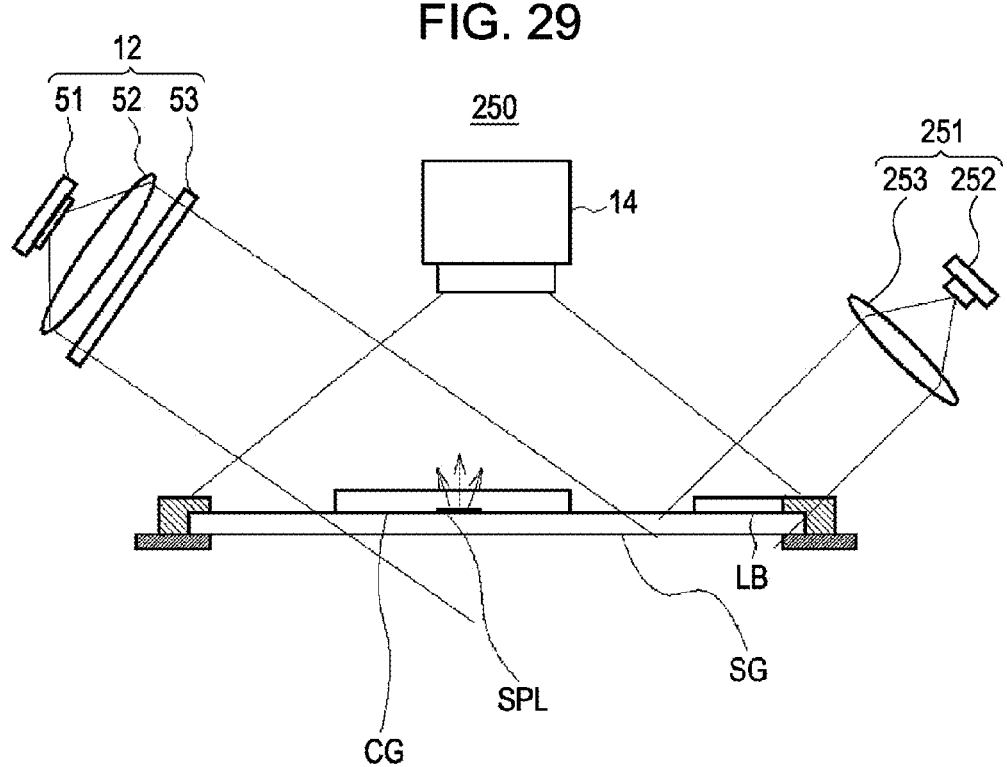
FIG. 29 is a diagram schematically illustrating a configuration of a dark field illumination system of a thumbnail image taking unit (7) according to another embodiment.

In the second embodiment described above, there has been described the case where the white illumination system 211 illuminates the entire slide glass SG. The present application is not limited thereto, but, as in a thumbnail image taking unit 250 as shown in FIG. 29, a white LED 252 of a white illumination system 251 may illuminate only the label LB via a condenser 253.

Figure 30:
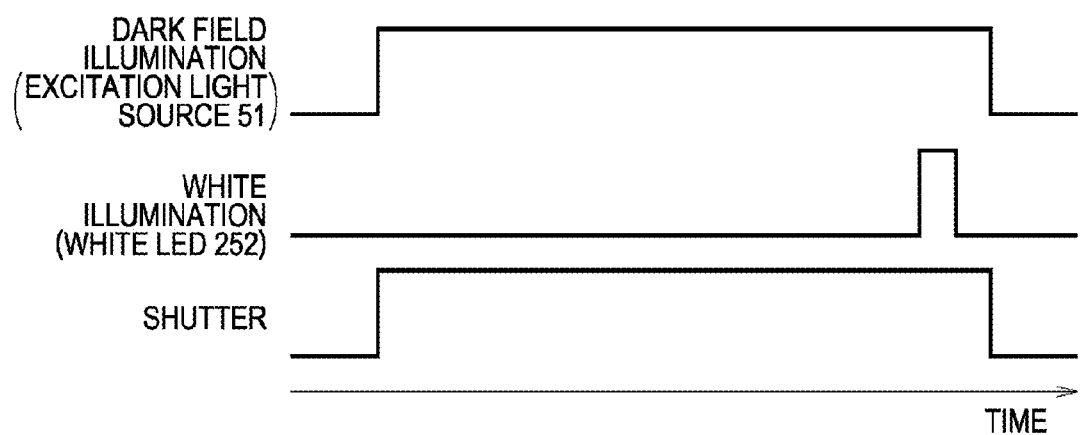
FIG. 30 is a diagram illustrating timing charts for the control of a light source and a shutter.

In this case, the light source control unit 72 and the thumbnail image obtaining unit 73 irradiate the excitation light from the excitation light source 51 to the entire slide glass SG and simultaneously make a shutter of the thumbnail camera 14 open, in accordance with timing charts shown in FIG. 30.

Next, the light source control unit 72 drives the white LED 252 of the white illumination system 251 at a predetermined timing for a sufficiently short time as compared with the excitation light source 51. This prevents the biological sample SPL part from being imaged in white color by the white light due to the irradiation of the white light for a long time, since an intensity of the white light emitted from the white LED 252 is greater than that of the coloring light emitted by DAPI marked on the biological sample SPL.

Thereafter, the light source control unit 72 and the thumbnail image obtaining unit 73 finish driving the excitation light source 51 and simultaneously make the shutter of the thumbnail camera 14 closed.

Figure 31:
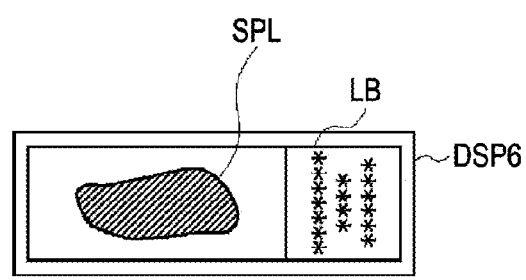
FIG. 31 is an outlined line diagram illustrating a dark field thumbnail image (6) according to the second embodiment.

In this way, the thumbnail image obtaining unit 73 obtains, as shown in FIG. 31, a dark field thumbnail image DSP6 containing the fluorescently excited biological sample SPL and label LB.

Therefore, the biological sample image obtaining device 200 can obtain the dark field thumbnail image DSP6 where the outer shape of the biological sample SPL can be recognized and the written contents of the label LB can also be recognized.

3. Third Embodiment

In the third embodiment, obtaining the dark field thumbnail image will be described, and obtaining the bright field thumbnail image, the bright field enlarged image, and the dark field enlarged image is the same as that in the first embodiment, and thus the description thereof will be omitted.

Like the first and second embodiments, when the dark field thumbnail image is taken in the dark field mode, it sometimes occurs that the excitation light is reflected from edges of the slide glass SG and then reaches the thumbnail camera 14. In addition, it sometimes occurs that when fluorescent materials included in other stains, remnants after cleaning, dusts, finger prints or the like are attached on the slide glass SG, fluorescence is emitted by excitation due to the excitation light.

Figure 32:
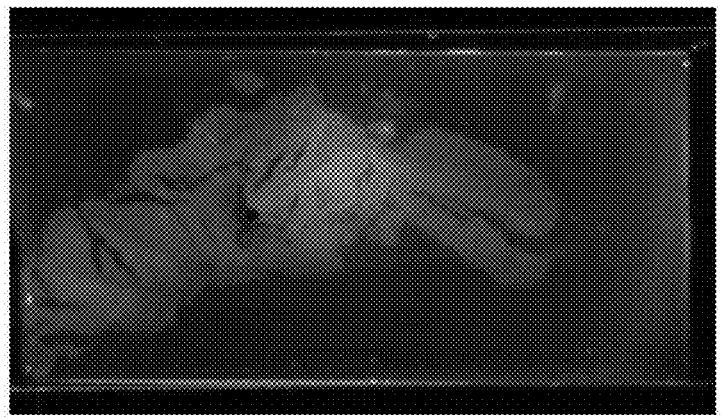
FIG. 32 is a diagram illustrating a dark field thumbnail image including noise.

In such a case, as an example is shown in FIG. 32 (refer to FIG. 1), there is obtained a dark field thumbnail image where the excitation light reflected from the edges of the slide glass SG looks like, for example, a red color, and fluorescent materials other than DAPI are excited by the excitation light to emit, for example, a green color. Such light emitted from materials other than DAPI is a noise in recognizing the outer shape of the biological sample SPL.

Thereby, in the dark field thumbnail image containing the noise, it is thought that the outer shape of the biological sample SPL is not accurately recognized by the noise. Particularly, in a case where an intensity of the coloring light emitted from DAPI is low and the coloring light from DAPI fails to be contained in the dark field thumbnail image in sufficient brightness, the strong influence of the noise hinders the recognition of the outer shape of the biological sample SPL.

In the third embodiment, there is obtained a dark field thumbnail image where the outer shape of the biological sample SPL can be accurately recognized from the dark field thumbnail image.

In addition, a biological sample image obtaining device according to the third embodiment has the same configuration as the biological sample image obtaining devices 1 and 200 (FIG. 1) in the first and second embodiments as a whole, and may employ all of the thumbnail image taking units described above. Hereinafter, a case of employing the biological sample image obtaining device 1 will be described.

3-1. Configuration of Thumbnail Camera

Figure 33:
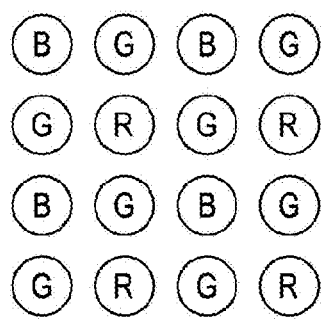
FIG. 33 is an outlined line diagram illustrating the Bayer arrangement in a color filter.

The thumbnail camera 14 is provided with color filters at a front face of the imaging area. For the color filters, as shown in FIG. 33, filters of red R, green G, and blue B for the respective pixels of the imaging element are disposed in the Bayer arrangement. The pixels provided with the filters of red R, green G, and blue B are also referred to as red pixels, green pixels, and blue pixels, respectively.

3-2. Detailed Contents of Biological Sample Image Obtaining Processing

When receiving a command for obtaining an image of the biological sample SPL from the operation input unit 64, the CPU 61 develops a program corresponding to the command in the RAM 63.

The CPU 61 functions as the stage movement control unit 71, the light source control unit 72, the thumbnail image obtaining unit 73, the region designation unit 74, the enlarged image obtaining unit 75, and the data recording unit 76, in accordance with the program corresponding to the command for obtaining an image of the biological sample SPL, as shown in FIG. 6.

The light source control unit 72 drives the excitation light source 51 when the dark field mode is selected. The thumbnail image obtaining unit 73 images the entire slide glass SG by using the thumbnail camera 14 in the state where the excitation light emitted from the excitation light source 51 is irradiated.

The thumbnail image obtaining unit 73 converts pixel values (luminance values) for the red pixels and green pixels into 0, of image signals obtained from the respective pixels when the thumbnail camera 14 images the entire slide glass SG.

Also, the thumbnail image obtaining unit 73 performs an image processing such as, for example, a bilinear interpolation, or the like, for image signals having values obtained when the pixel values (luminance values) for the red pixels and green pixels are converted into 0 and only pixel values for the blue pixels are imaged, and generates a dark field thumbnail image.

Figure 34:
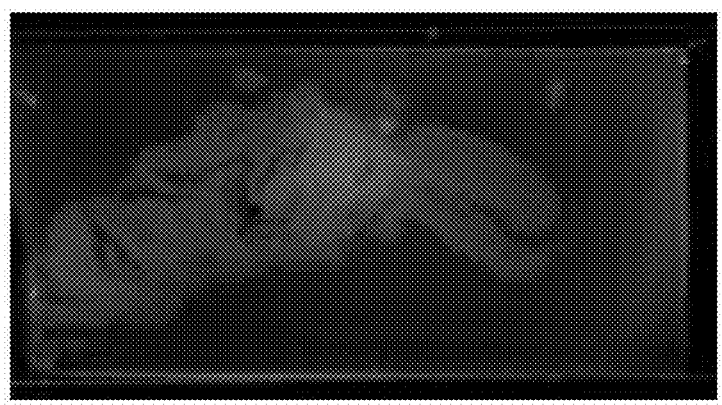
FIG. 34 is a diagram illustrating a dark field thumbnail image where the noise is removed.

FIG. 34 (refer to FIG. 2) shows an example of the dark field thumbnail image generated by the thumbnail image obtaining unit 73. As can be seen from the dark field thumbnail image, the red part or the green part is removed from the dark field thumbnail image shown in FIG. 32, and a noise is reduced.

In this way, the biological sample image obtaining device 1 obtains the dark field thumbnail image where the outer shape of the fluorescently stained biological sample SPL can be accurately recognized.

3-3. Operation and Effect

The biological sample image obtaining device 1 with the above-described configuration emits the excitation light from the excitation light source 51 so that the fluorescent material (probe) marked on the target in the biological sample SPL lies in the non-excited state and the fluorescent material (DAPI) marked on the control with the probe lies in the excited state.

The biological sample image obtaining device 1 generates the dark field thumbnail image where only the color component of the fluorescence emitted by the fluorescent material (DAPI) marked on the control with the probe is extracted from the color image of the entire slide glass SG imaged by the thumbnail camera 14.

Thereby, the biological sample image obtaining device 1 can remove from the dark field thumbnail image a noise caused by the excitation light reflected from the edges of the slide glass SG or a noise such as fluorescence or the like emitted by the excitation of fluorescent materials included in stains other than DAPI, remnants after cleaning, dusts, fingerprint or the like.

Therefore, the biological sample image obtaining device 1 can obtain the dark field thumbnail image where the outer shape of the fluorescently stained biological sample SPL can be accurately recognized.

3-4. Other Embodiments

In the third embodiment described above, there has been described the case where the dark field thumbnail image is generated by irradiating the excitation light to the region where the biological sample SPL is disposed.

The present application is not limited thereto, but, like the second embodiment, the dark field thumbnail image may be generated from the excitation light thumbnail image obtained by irradiating the excitation light and imaging, and the white light thumbnail image obtained by irradiating the white light and imaging.

In this case, the biological sample image obtaining device 200 is used, and the thumbnail image obtaining unit 73 performs the image processing using only the blue pixel values for image signals obtained by irradiating the excitation light and imaging, and generates the excitation light thumbnail image.

In addition, the thumbnail image obtaining unit 73 obtains the white light thumbnail image WSP where the label LB part obtained by irradiating the white light is lighted. The thumbnail image obtaining unit 73 generates the dark field thumbnail image including at least the biological sample SPL part in the excitation light thumbnail image and the label LB part in the white light thumbnail image as in the second embodiment.

In the third embodiment described above, there has been described the case of employing the thumbnail camera 14 where the filters of red R, green G, and blue B for the respective pixels of the imaging element are disposed in the Bayer arrangement. The present application is not limited thereto, but it may be employed that filters of red R, green G, and blue B for the respective pixels of the imaging element are disposed in other arrangements.

In the third embodiment described above, there has been described the case where the dark field thumbnail image is generated by converting the pixel values for the red pixels and green pixels into 0 and performing the image processing using only the pixel values for the blue pixels, of the image signals obtained from the thumbnail camera 14.

The present application is not limited thereto, but the dark field thumbnail image may be generated by using pixel values for all of the pixels of image signals obtained from the thumbnail camera 14, and an image processing for removing color components of red and green may be performed for the dark field thumbnail image.

In relation thereto, the case where the pixel values for the red pixels and green pixels are converted into 0 and the dark field thumbnail image is generated by using only the pixel values for the blue pixels can further reduce the noise than the case where the dark field thumbnail image is generated by using the pixel values for all of the pixels and thereafter the image processing for removing the color components of red and green is performed.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fluorescent image obtaining device comprising:
   a light source that irradiates light such that a fluorescent material marked on a target in a biological sample lies in a non-excited state and a fluorescent material marked on a control with the target lies in an excited state; and
   an imaging unit that takes an image including the entire biological sample,
   wherein the imaging unit comprises an imaging element; and color filters that are disposed at a front face of the imaging element, where a plurality of different color filters are disposed in a predetermined arrangement for respective pixels of the imaging element, and
   wherein an obtaining unit generates an image having only a color component of fluorescence emitted by the fluorescent material marked on the control with the target, from a color image taken by the imaging unit.

2. A fluorescent image obtaining device according to claim 1, further comprising:
   a designation unit that designates a region that is to be imaged as an enlarged image of the biological sample based on the excited state of the second fluorescent material marked on the control with the target, the region including a plurality of imaging regions that are to be individually imaged.

3. The fluorescent image obtaining device according to claim 1, further comprising:
   a white light source that is provided at an opposite surface side of a support body where the biological sample is disposed, to the imaging unit and emits a white light; and
   a diffusion plate that is provided between the support body and the white light source and diffuses the white light emitted from the white light source to be irradiated to the biological sample.

4. The fluorescent image obtaining device according to claim 3, wherein the light source is provided at the same surface side of the support body as the imaging unit, irradiates the light to the biological sample with a tilted angle larger than about a half of an angle of view of the imaging unit with respect to an optical axis of the imaging unit, and irradiates the light to a range exceeding an imaging range of the imaging unit.

5. The fluorescent image obtaining device according to claim 1, wherein the light source is provided at an opposite surface side of the support body to the imaging unit, irradiates the light to the biological sample with a tilted angle larger than about a half of an angle of view of the imaging unit with respect to an optical axis of the imaging unit, and irradiates the light to parts other than an imaging area of the imaging unit.

6. The fluorescent image obtaining device according to claim 3, wherein the light source is provided at a lateral surface side of the support body to irradiate the light to the lateral surface, and irradiates the light to the biological sample via an inside of the support body.

7. The fluorescent image obtaining device according to claim 3, further comprising a support unit that supports the support body,
   wherein the light source is provided inside the support unit to irradiate light to a lateral surface of the support body, and irradiates the light to the biological sample via an inside of the support body.

8. The fluorescent image obtaining device according to claim 1, further comprising:
   a white light source that is provided at a predetermined position in which the support body where the biological sample is disposed is placed, and irradiates a white light to a region where information for the biological sample is given; and
   wherein the obtaining unit that obtains a dark field image, including the entire biological sample, taken by the imaging unit in a state where the light source irradiates light to the biological sample, and obtains a bright field image, including the entire biological sample, taken by the imaging unit in a state where the white light source irradiates the white light to the region.

9. The fluorescent image obtaining device according to claim 8, wherein the obtaining unit generates an image by combining the obtained dark field image and bright field image.

10. The fluorescent image obtaining device according to claim 8, wherein the obtaining unit extracts a biological sample part from the dark field image, extracts a region part from the bright field image, and generates an image where the extracted biological sample part and the extracted region part are combined.

11. The fluorescent image obtaining device according to claim 8, wherein the obtaining unit detects an outer shape of the biological sample from the dark field image and generates a profile image indicating the outer shape.

12. The fluorescent image obtaining device according to claim 11, wherein the obtaining unit synthesizes information indicating an outer shape of the biological sample based on the profile image with the bright field sample image.

13. The fluorescent image obtaining device according to claim 1, wherein the obtaining unit generates an image including the entire biological sample based on a signal of only the color component of fluorescence emitted by the fluorescent material marked on the control with the target in the imaging element of the imaging unit.

14. The fluorescent image obtaining device according to claim 1, further comprising an enlarged image obtaining unit to position the biological sample and magnify imaging of the biological sample to individually image each of the plurality of imaging regions.

15. The fluorescent image obtaining device according to claim 14, wherein the fluorescent image obtaining device obtains an enlarged image of the biological sample in the image by combining the images of the plurality of imaging regions.

16. A fluorescent image obtaining method comprising:
   irradiating light from a light source such that a fluorescent material marked on a target in a biological sample lies in a non-excited state and a fluorescent material marked on a control with the target lies in an excited state; and
   taking an image including the entire biological sample by an imaging unit,
   wherein the imaging unit comprises an imaging element and color filters that are disposed at a front face of the imaging element, where a plurality of different color filters are disposed in a predetermined arrangement for respective pixels of the imaging element, and
   wherein an obtaining unit generates an image having only a color component of fluorescence emitted by the fluorescent material marked on the control with the target, from a color image taken by the imaging unit.

17. A machine-readable device having instructions stored thereon, which when executed, cause a computer to:
   irradiate light from a light source such that a fluorescent material marked on a target in a biological sample lies in a non-excited state and a fluorescent material marked on a control with the target lies in an excited state; and
   take an image including the entire biological sample by an imaging unit,
   wherein the imaging unit comprises an imaging element and color filters that are disposed at a front face of the imaging element, where a plurality of different color filters are disposed in a predetermined arrangement for respective pixels of the imaging element, and
   wherein an obtaining unit generates an image having only a color component of fluorescence emitted by the fluorescent material marked on the control with the target, from a color image taken by the imaging unit.

* * * * *